(12) United States Patent
Kasuya et al.

(10) Patent No.: US 11,142,636 B2
(45) Date of Patent: Oct. 12, 2021

(54) (METH)ACRYLATE COMPOUND, ADDITIVE FOR OPTICAL RESIN, OPTICAL ELEMENT, AND OPTICAL DEVICE

(71) Applicant: NIKON CORPORATION, Tokyo (JP)

(72) Inventors: Masakatsu Kasuya, Chiba (JP); Yosuke Inokuchi, Tokyo (JP); Shiho Nishimura, Sagamihara (JP); Toru Nakamura, Kawasaki (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 16/459,923

(22) Filed: Jul. 2, 2019

(65) Prior Publication Data
US 2019/0322857 A1    Oct. 24, 2019

Related U.S. Application Data

(63) Continuation of application No. PCT/JP2017/001357, filed on Jan. 17, 2017.

(51) Int. Cl.
*C08L 33/14*        (2006.01)
*C08L 33/10*        (2006.01)
(Continued)

(52) U.S. Cl.
CPC ............ *C08L 33/14* (2013.01); *C08L 33/10* (2013.01); *G02B 1/041* (2013.01); *G02B 5/1876* (2013.01)

(58) Field of Classification Search
CPC ......... C08L 33/14; C08L 33/10; G02B 1/041; G02B 5/1876
(Continued)

(56) References Cited

U.S. PATENT DOCUMENTS

| 2001/0016093 A1 | 8/2001 | Dawes et al. |
| 2002/0048639 A1 | 4/2002 | Negoro et al. |

(Continued)

FOREIGN PATENT DOCUMENTS

| CN | 102498138 A | 6/2012 |
| EP | 0 093 856 A1 | 11/1983 |

(Continued)

OTHER PUBLICATIONS

Guo et al., "Preparation and characterization of acrylates and polyacrylates having variable fluorine contents and distributions"; Journal of Polymer Science Part A: Polymer Chemistry, vol. 32, No. 1, Jan. 15, 1994 pp. 475-481.*

(Continued)

*Primary Examiner* — William K Cheung
(74) *Attorney, Agent, or Firm* — Staas & Halsey LLP

(57) ABSTRACT

Provided is an additive for an optical resin including a (meth)acrylate compound represented by general formula (1) below:

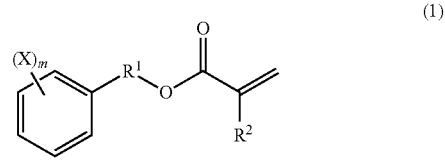

[in general formula (1), each X independently represents a fluorine atom or a methyl group in which at least one hydrogen atom is substituted with a fluorine atom; m represents an integer of 0 to 5; $R^1$ represents an alkylene group (Continued)

or an oxyalkylene group having a carbon number of 1 to 8; and $R^2$ represents a hydrogen atom or a methyl group].

12 Claims, 14 Drawing Sheets

(51) Int. Cl.
   *G02B 1/04* (2006.01)
   *G02B 5/18* (2006.01)

(58) Field of Classification Search
   USPC .......................................................... 524/556
   See application file for complete search history.

(56) References Cited

U.S. PATENT DOCUMENTS

| | | | |
|---|---|---|---|
| 2003/0022103 A1 | 1/2003 | Lee et al. | |
| 2005/0014088 A1 | 1/2005 | Nakamura et al. | |
| 2008/0090027 A1 | 4/2008 | Li et al. | |
| 2008/0094712 A1 | 4/2008 | Miyakawa | |
| 2012/0309863 A1 | 12/2012 | Miyakawa | |
| 2013/0004676 A1* | 1/2013 | Ha | C08F 220/30 427/508 |
| 2014/0178818 A1 | 6/2014 | Hatakeyama | |
| 2015/0018445 A1 | 1/2015 | Iizuka et al. | |

FOREIGN PATENT DOCUMENTS

| | | |
|---|---|---|
| EP | 1 258 742 A1 * | 11/2002 |
| JP | 1-234406 | 9/1989 |
| JP | 2002-98828 | 4/2002 |
| JP | 2003-55408 | 2/2003 |
| JP | 2003-519819 | 6/2003 |
| JP | 2003-523528 | 8/2003 |
| JP | 2008-111110 | 5/2008 |
| JP | 2008-203821 | 9/2008 |
| JP | 2009-79225 | 4/2009 |
| JP | 2010-7004 | 1/2010 |
| JP | 2010-37525 | 2/2010 |
| JP | 2013-10864 A | 1/2013 |
| JP | 2013-204034 | 1/2013 |
| JP | 2013-49823 | 3/2013 |
| JP | 2013-155245 A | 8/2013 |
| JP | 2013-227392 | 11/2013 |
| JP | 2014-108983 | 6/2014 |
| JP | 2014-122949 | 7/2014 |
| JP | 2016-98248 | 5/2016 |
| KR | 10-2012-0061427 | 6/2012 |
| WO | 2006/068137 A1 | 6/2006 |
| WO | 2008/018336 A1 | 2/2008 |
| WO | WO 2011/010633 A1 | 1/2011 |
| WO | WO 2016/031249 A1 | 3/2016 |

OTHER PUBLICATIONS

Japanese Office Action dated Apr. 28, 2020 in Japanese Patent Application No. 2018-562748.
V. D. Athawale et al., "Syntheses of Optically Active Polyacrylates" Journal of Macromolecular Science—Pure and Applied Chemistry, vol. A35, No. 6, Jan. 25, 1998, pp. 985-1001, (Table 2.) (18 pages).
Eiji Yamamoto et al., "Development and Analysis of a Pd(0)-Catalyzed Enantioselective 1,1-Diarylation of Acrylates Enabled by Chiral Anion Phase Transfer" Journal of the American Chemical Society, 2016 138, 15877-15880 (Figure 2.), (Published Nov. 22, 2016) (4 pages).
Haruumi Hasuo et al, "Development of High-performance Normal Mode Type (Polymer/Liquid Crystal) Composite Films using UV curable monomers" Heisei 13 Nendo Fukuoka-Ken Kogyo Gijutsu Center Kenkyu Hokoku (No. 12), 2001, Hobun 4., 14 to 17, tables 1, 2, 3-1 Tankanno Hikari Jugosei Monomer-shu no Eikyo (4 pages).
Masahiro Yamaguchi et al., "Design of (Ploymer/Liquid Crystal) Composite Films Using UV Curable Acrylate Monomer" Heisei 11 Nendo Fukuoka-Ken Kogyo Gijutsu Center Kenkyu Hokoku (No. IO), 1999, note 14., 55 to 57, fig. 1, 2, table 1 (3 pages).
International Search Report dated Mar. 7, 2017 in corresponding International Patent Application No. PCT/JP2017/001357 (7 pages).
Extended European Search Report dated Oct. 15, 2020 in European Patent Application No. 17892595.4.
H. Kaye et al.; "Magnetic circular dichroism studies of aromatic polymers", Journal of Polymer Science, Polymer Chemistry Edition, vol. 18, Oct. 1, 1980, pp. 2993-3008.
Andrew Guo et al., "Preparation and characterization of acrylates and polyacrylates having variable fluorine contents and distributions"; Journal of Polymer Science Part A: Polymer Chemistry, vol. 32, No. 1, Jan. 15, 1994, pp. 47-56.
Mao et al., "Quantitative analysis of copolymers by FTIR"; European Polymer Journal, vol. 29, No. 4, Apr. 1, 1993, pp. 475-481.
First Office Action dated Jun. 9, 2021 in Chinese Patent Application No. 201780078969.2.
Shigeru Hirabayashi et al.; "Improvements to Light Transmittance in Light-cured Composite Resins by the Utilisation of Low Refractive Index Dimethacrylates"; Dental Materials Journal 9 (2) 203-214, 1990; received on Jul. 26, 1990.

* cited by examiner

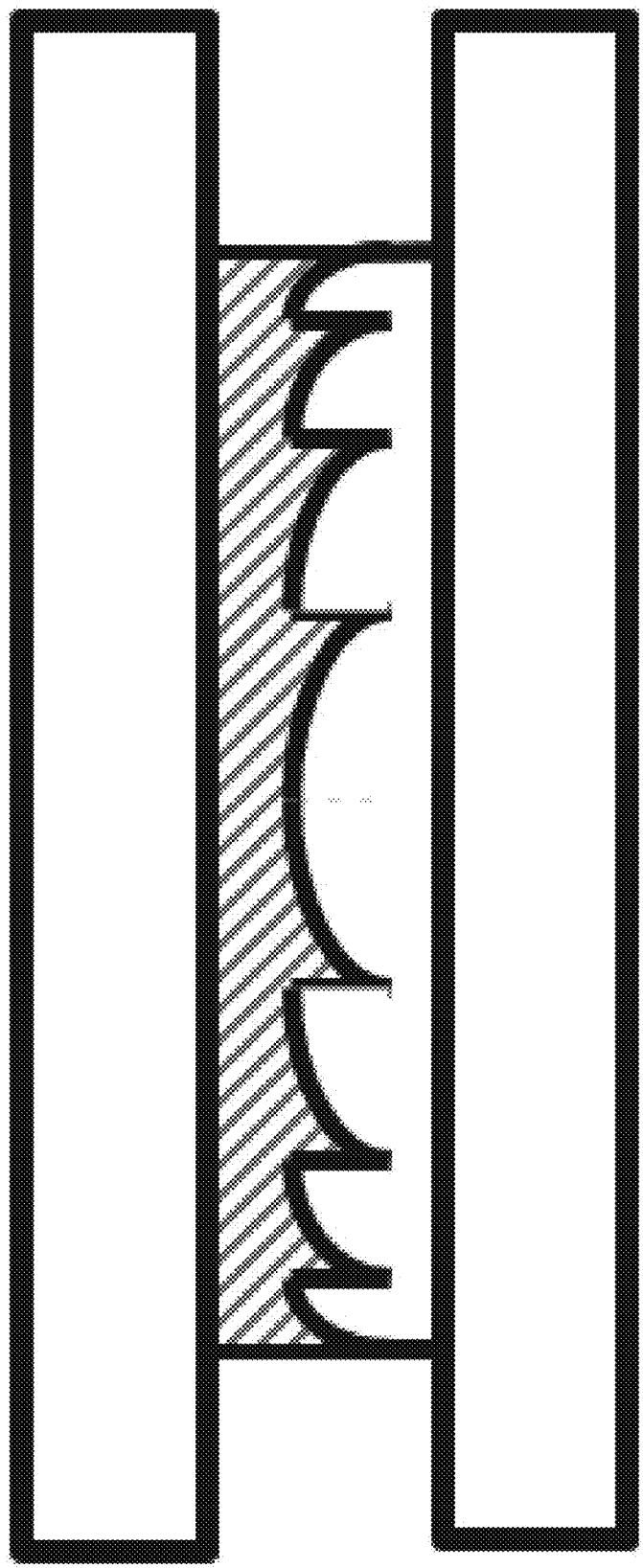

(METH)ACRYLATE COMPOUND, ADDITIVE FOR OPTICAL RESIN, OPTICAL ELEMENT, AND OPTICAL DEVICE

CROSS-REFERENCE TO RELATED APPLICATIONS

This application is a Continuation Application, under 35 U.S.C. § 111(a), of International Patent Application No. PCT/JP2017/001357, filed on Jan. 17, 2017, the entire content of which is incorporated herein by reference.

TECHNICAL FIELD

The present invention relates to a compound used for optical applications.

BACKGROUND ART

In recent years, a diffractive optical element (DOE) in which the traveling direction of light is changed by utilizing a diffraction phenomenon has attracted attention. For example, a transmissive blaze-type diffractive optical element has an excellent feature that all incident light can focus only in a desired direction (a specific diffraction order). Moreover, contact multilayer phase Fresnel lenses in which the diffractive optical element is combined with a general glass lens have been developed by utilizing a property that generates strong chromatic aberration in the opposite direction to the direction of the refractive optical element having a refractive surface.

However, the diffractive optical element causes a problem that diffracted light other than diffracted light having a desired diffraction order is unnecessary light and thus a blurred image is generated to increase the amount of generated flare. Conventionally, in order to reduce such flare and to obtain a constitution having high diffraction efficiency in a wide wavelength range, a combination of a diffractive optical element made of a resin raw material having relatively low refraction and high dispersion and a diffractive optical element made of a resin raw material having high refraction and low dispersion has tended to be used. Moreover, use of a composite material obtained by dispersing inorganic fine particles has been tried as a resin material of the diffractive optical element (for example, Patent Literature 1).

CITATION LIST

Patent Literature

PTL 1: JP 2008-203821A

SUMMARY OF INVENTION

Technical Problem

However, a sufficient flare reduction effect is difficult to obtain even when the techniques described above are applied, and the more complex the shape of a grating becomes, the more likely another arises in a molding step. Namely, the problem is that, in general, a low refraction and high dispersion resin raw material frequently has a high viscosity and addition of fine particles or the like in order to improve the optical properties causes a relative increase in viscosity, and thus the resin cannot correspond to a relief pattern during molding. In particular, the resin raw material having high viscosity is difficult to fill into fine mold grooves, and thus a fine relief pattern may not be formed.

The inventors of the present invention have searched for utilizable compounds serving as a material that imparts excellent processing properties with respect to a resin raw material. As a result, the inventors of the present invention have found a compound group that can improve the processing properties without impairing optical properties after processing when the compound is added to a resin raw material and have completed embodiments of the present invention.

An embodiment of the present invention is an additive for an optical resin including a compound represented by general formula (1) below.

[Chemical Formula 1]

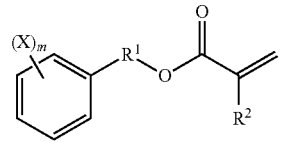

(1)

[In general formula (1), each X independently represents a fluorine atom or a methyl group in which at least one hydrogen atom is substituted with a fluorine atom; m represents 0; $R^1$ represents an alkylene group or an oxyalkylene group having a carbon number of 1 to 8; and $R^2$ represents a hydrogen atom or a methyl group].

DESCRIPTION OF EMBODIMENTS

Figure 1:
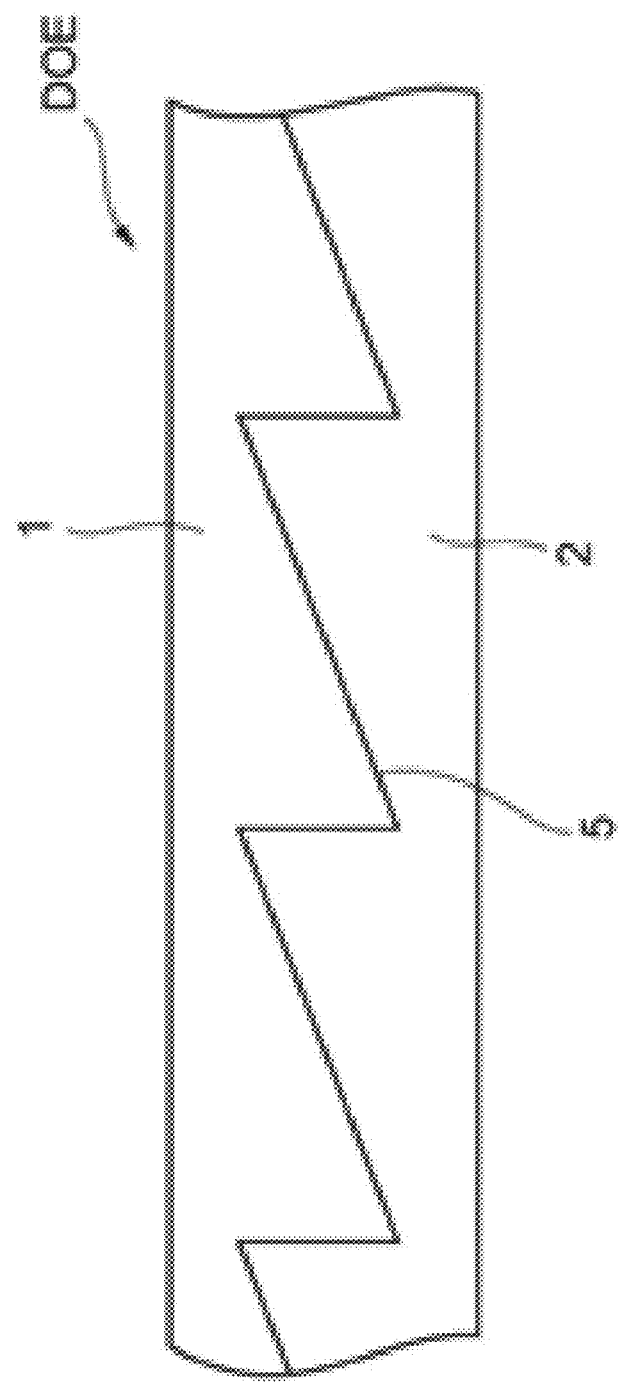
FIG. 1 is a sectional view of a structure example of a contact multilayer diffractive optical element (DOE).
Figure 2B:
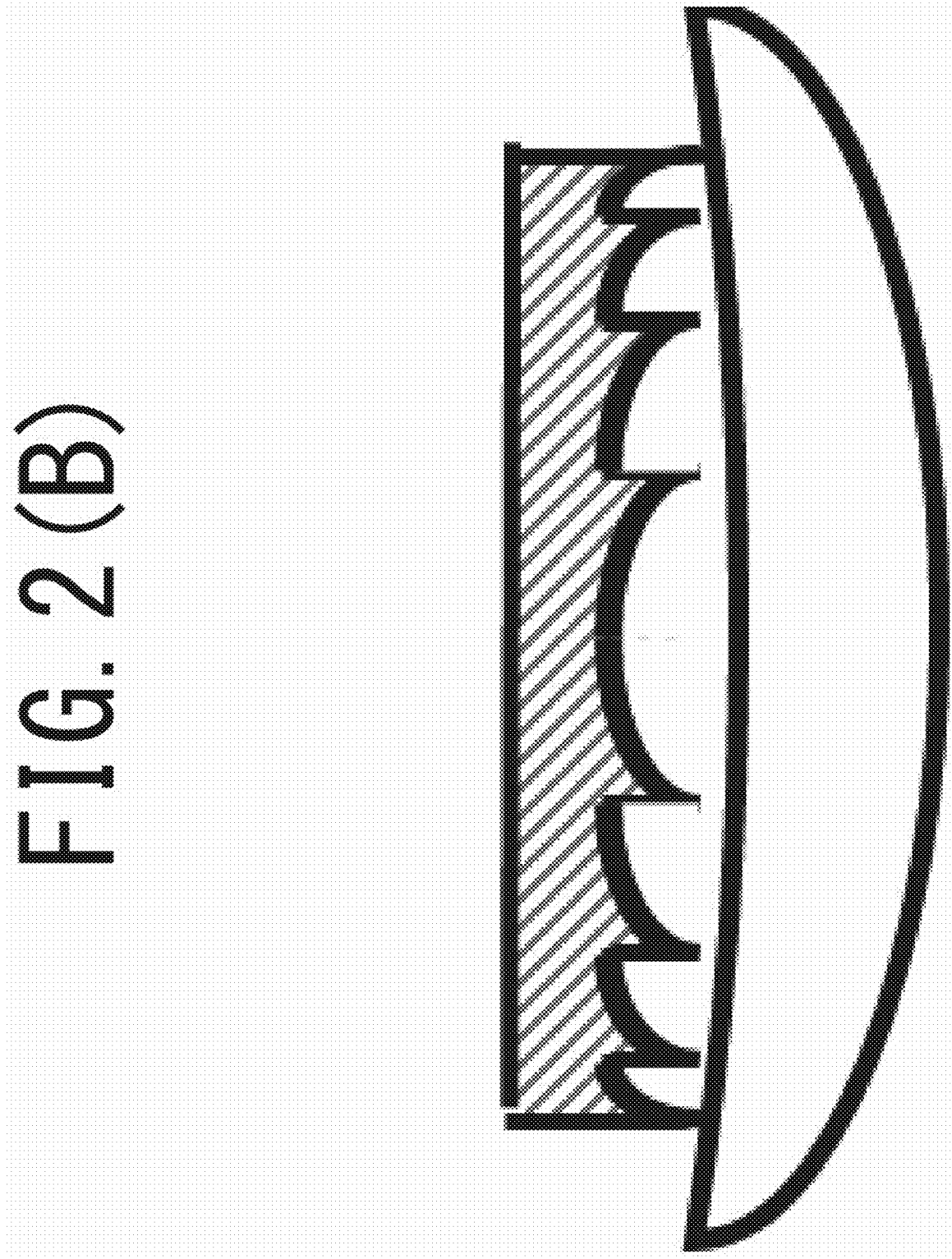
FIGS. 2A to 2I are sectional views of additional structure examples of the contact multilayer diffractive optical element (DOE).
Figure 2C:
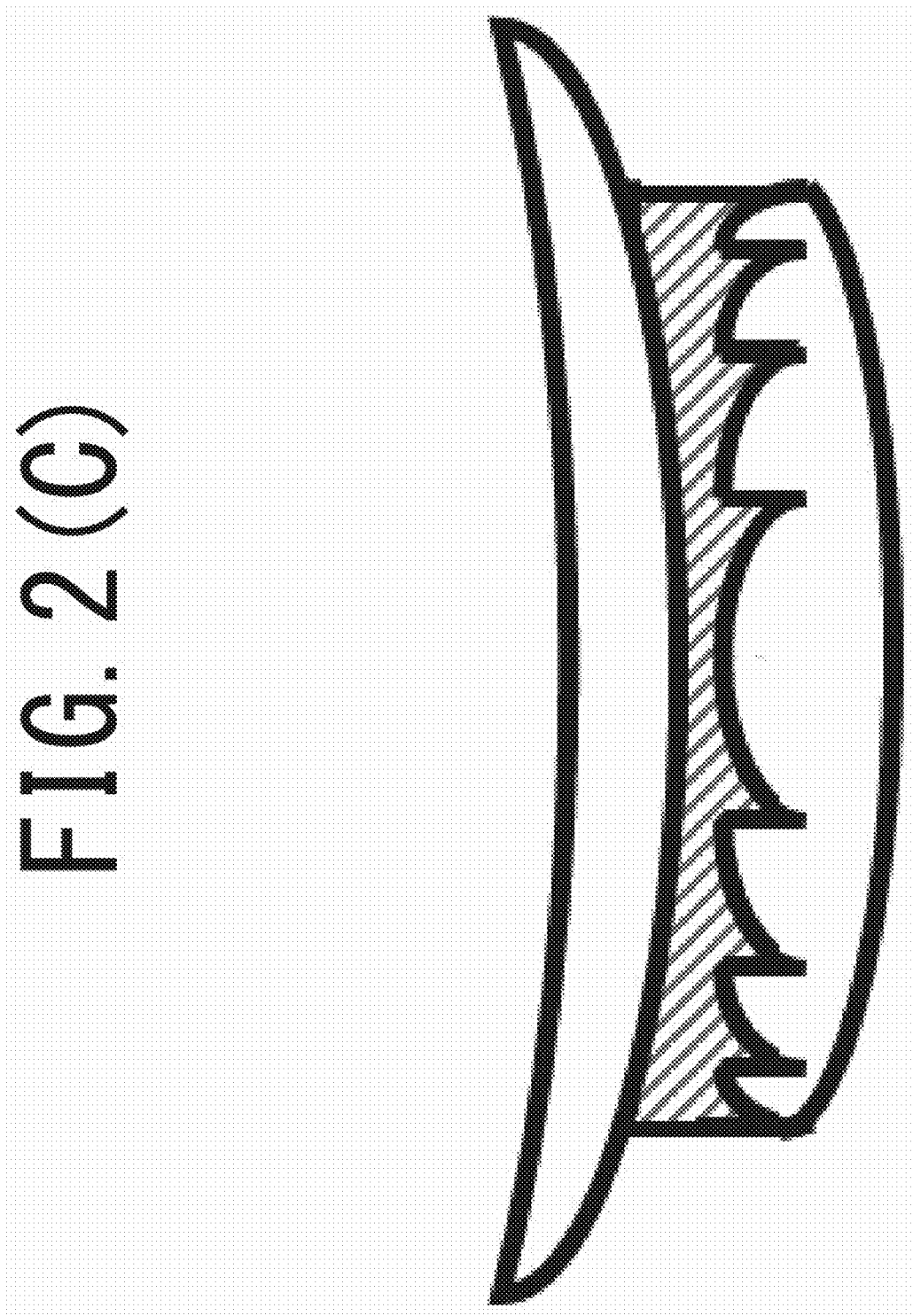
Figure 2D:
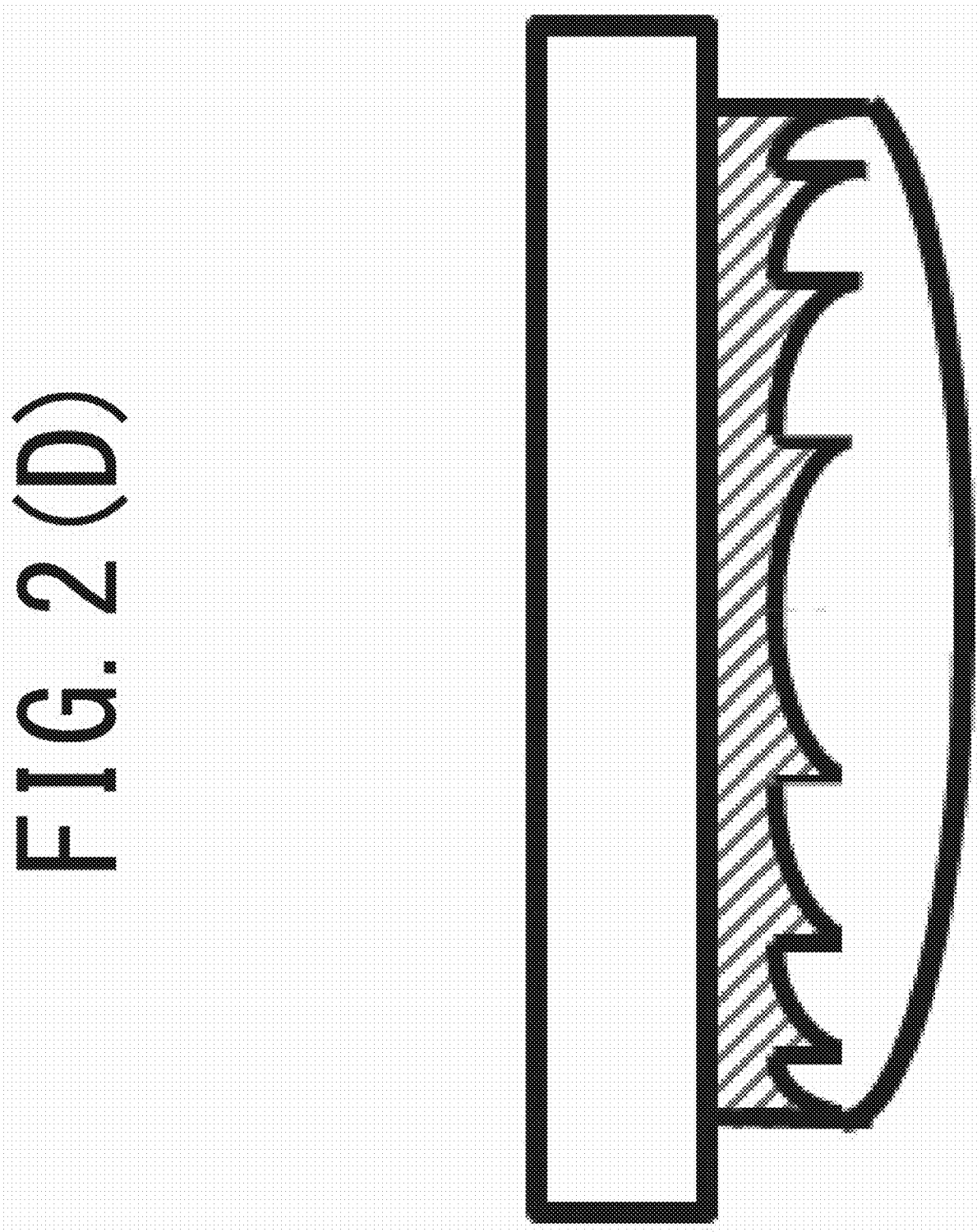
Figure 2E:
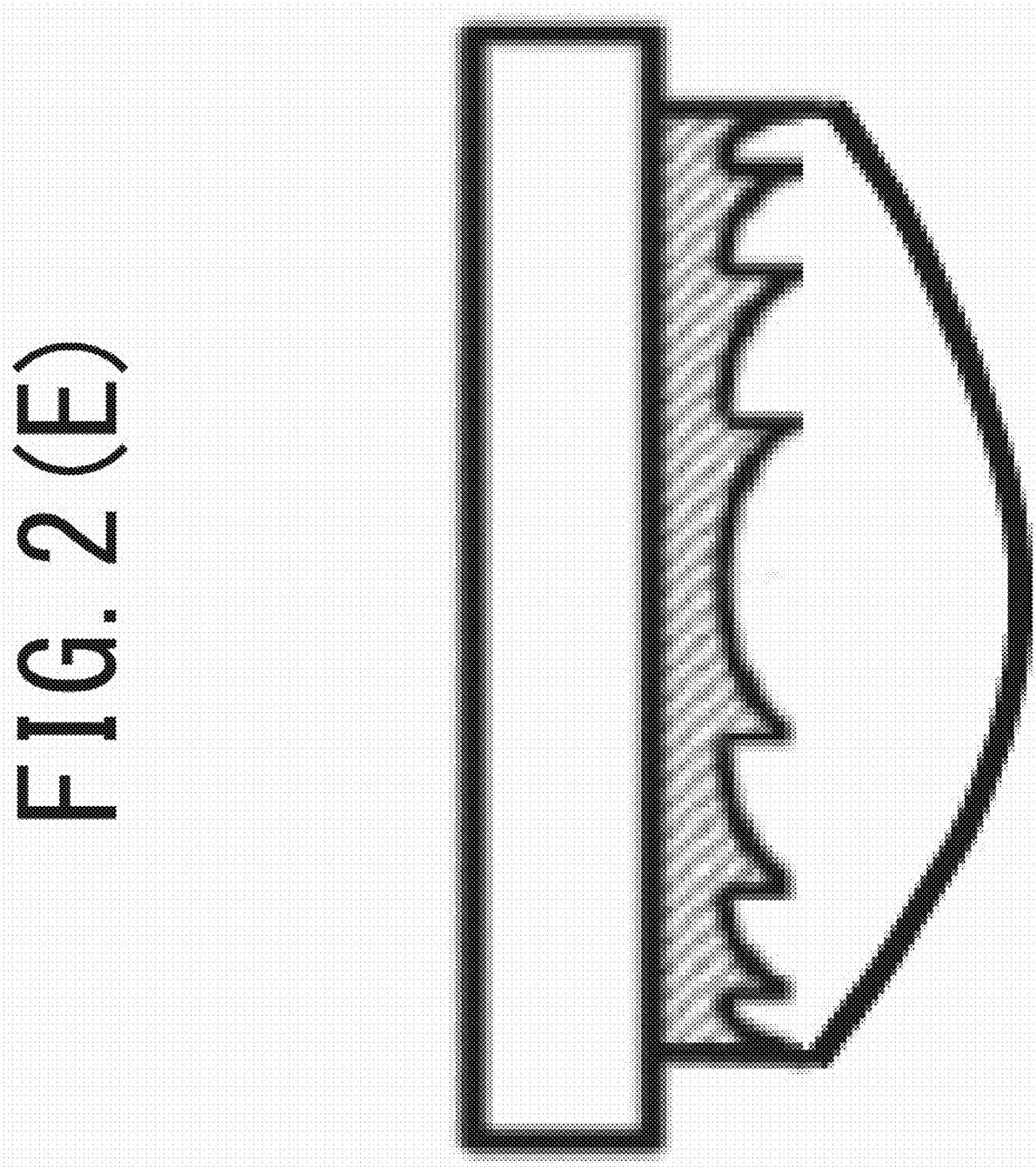
Figure 2F:
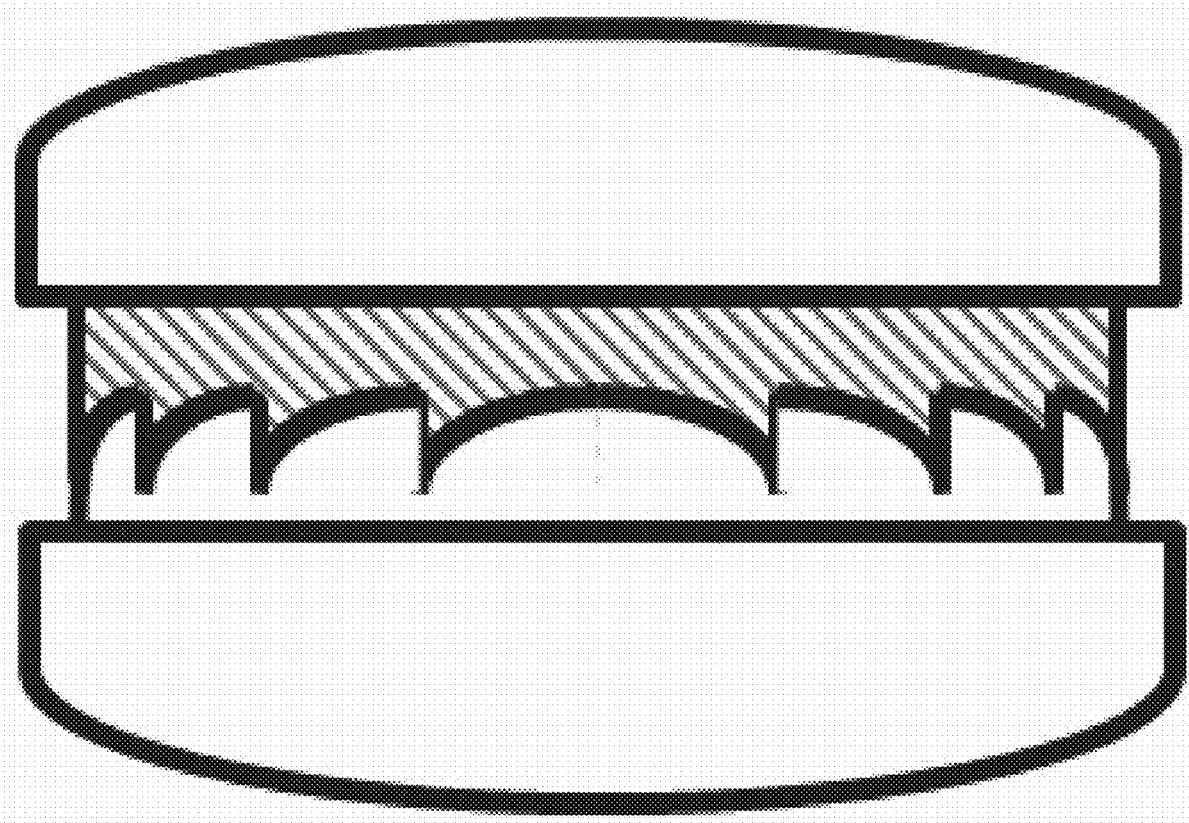
Figure 2:
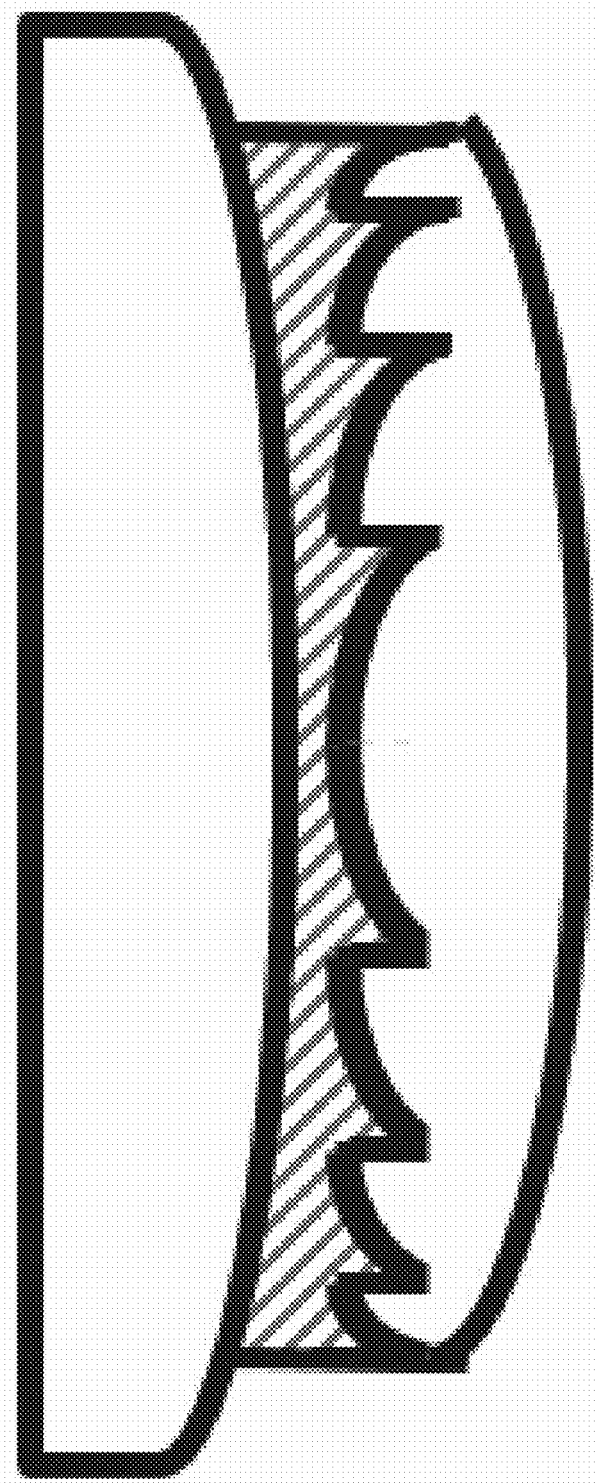
Figure 2H:
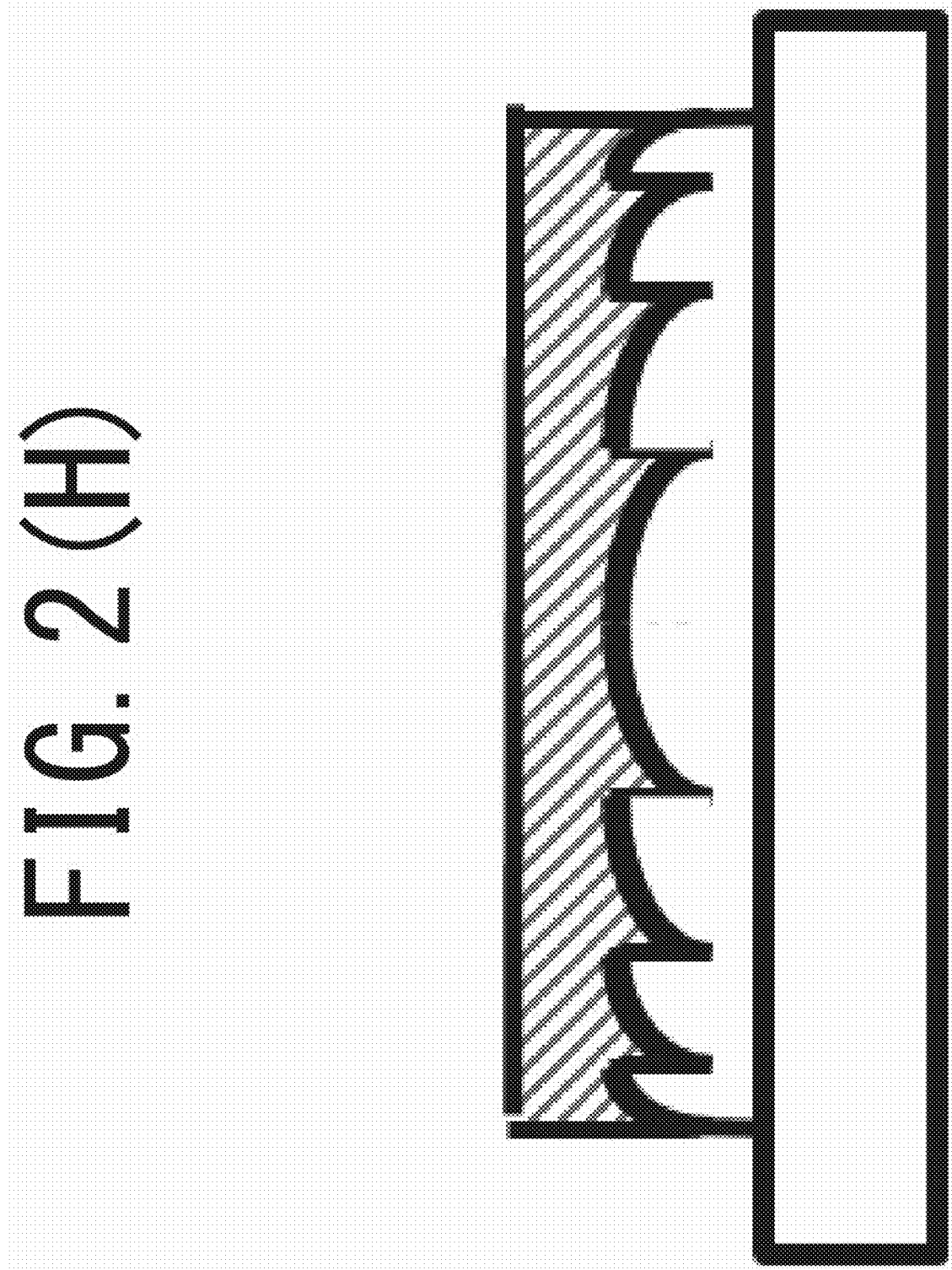
Figure 2I:
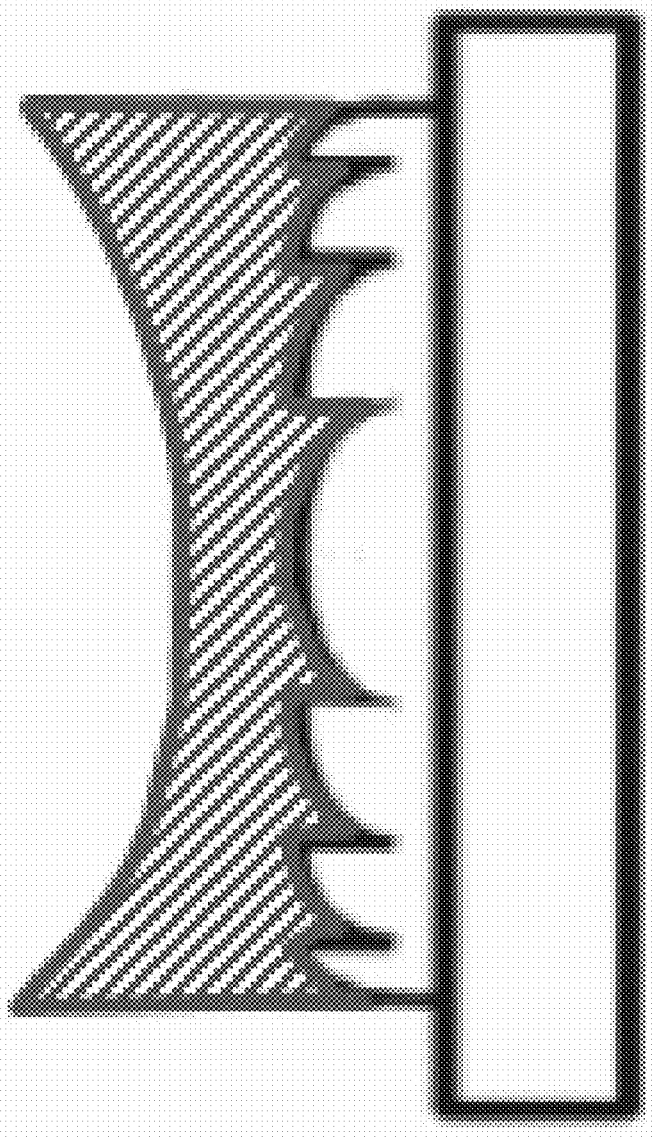

Hereinafter, embodiments of the present invention will be described in detail. Here, the embodiments of the present invention are not limited by these embodiments. In this specification, (meth)acrylate means acrylate and/or methacrylate, (meth)acrylated means acrylated and/or methacrylated, and (oxy)alkylene means alkylene and/or oxyalkylene.

<(a) (Meth)acrylate Compound>

A phenyl(oxy)alkylene (meth)acrylate compound (hereinafter, simply referred to as a (meth)acrylate compound) included in the additive according to the embodiment of the present invention includes at least one constitutional unit represented by general formula (1) below.

[Chemical Formula 2]

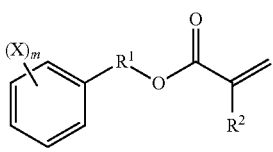

(1)

In general formula (1), each X independently represents a fluorine atom or a methyl group in which at least one hydrogen atom is substituted with a fluorine atom; m represents an integer of 0 to 5; $R^1$ represents an alkylene group or an oxyalkylene group having a carbon number of 1 to 8; and $R^2$ represents a hydrogen atom or a methyl group.

In general formula (1), examples of the substituent each independently represented by X include a fluorine atom and a methyl group in which at least one hydrogen atom is substituted with a fluorine atom. Specific examples of the methyl group in which at least one hydrogen atom is substituted with a fluorine atom include a monofluoromethyl group, a difluoromethyl group, and a trifluoromethyl group. Of these groups, the fluorine atom and the trifluoromethyl group are suitable.

In general formula (1), m represents an integer of 0 to 5. X is substituted at any position of the carbons located at substitutable five positions in the aromatic ring and the bonding position is not limited.

In general formula (1), the alkylene group or the oxyalkylene group represented by $R^2$ is preferably a linear, branched, or cyclic, alkylene group or oxyalkylene group having a carbon number of 1 to 8. Specific examples of the alkylene group having a carbon number of 1 to 8 include a methylene group, an ethylene group, an n-propylene group, an isopropylene group, an n-butylene group, and a t-butylene group. Specific examples of the oxyalkylene group having a carbon number of 1 to 8 include an oxymethylene group, an oxyethylene group, an oxy-n-propylene group, an oxy-isopropylene group, an oxy-n-butylene group, and an oxy-t-butylene group. Of these groups, the methylene group and the oxyethylene group are particularly preferable.

In general formula (1), $R^2$ represents a hydrogen atom or a methyl group.

A method for producing such a (meth)acrylate compound represented by general formula (1) is not particularly limited. For example, the compound can be produced as described below.

<Method for Producing (meth)acrylate Compound>

Of the (meth)acrylate compounds represented by general formula (1), in particular, a fluorine-containing phenylalkyl (meth)acrylate compound is which m is 1 to 5 and $R^1$ is an alkylene group is obtained, for example, using a fluorine-containing phenyl alcohol represented by general formula (2) below as a raw material.

[Chemical Formula 3]

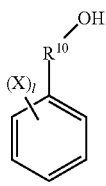

(2)

In general formula (2), each X independently represents a fluorine atom or a methyl group in which at least one hydrogen atom is substituted with a fluorine atom and 1 represents an integer of 1 to 5. $R^{10}$ represents an alkylene group having a carbon number of 1 to 8.

In general formula (2), each of the substituents independently represented by X represents a fluorine atom or a methyl group in which at least one hydrogen atom is substituted with a fluorine atom. Specific examples of the methyl group in which at least one hydrogen atom is substituted with a fluorine atom include a monofluoromethyl group, a trifluoromethyl group, and a trifluoromethyl group. Of these groups, the fluorine atom and the trifluoromethyl group are suitable.

In general formula (2), 1 represents an integer of 1 to 5. X substitutes at any positions of the carbons located at substitutable five positions in the aromatic ring and the bonding position is not limited.

In general formula (2), the alkylene group represented by $R^1$ is preferably a linear, branched, or cyclic alkylene group having a carbon number of 1 to 8. Specific examples of the alkylene group having a carbon number of 1 to 8 include a methylene group, an ethylene group, an n-propylene group, an isopropylene group, an n-butylene group, and a t-butylene group. Of these groups, the methylene group is particularly preferable.

Examples of such fluorine-containing phenyl alcohol compounds represented by general formula (2) include 2-fluorobenzyl alcohol, 3-fluorobenzyl alcohol, 4-fluorobenzyl alcohol, 2,3-difluorobenzyl alcohol, 2,4-difluorobenzyl alcohol, 2,5-difluorobenzyl alcohol, 2,6-difluorobenzyl alcohol, 3,4-difluorobenzyl alcohol, 3,5-difluorobenzyl alcohol, 3,6-difluorobenzyl alcohol, 2,3,4-trifluorobenzyl alcohol, 2,3,5-trifluorobenzyl alcohol, 2,3,6-trifluorobenzyl alcohol, 2,4,5-trifluorobenzyl alcohol, 2,4,6-trifluorobenzyl alcohol, 2,5,6-trifluorobenzyl alcohol, 3,4,5-trifluorobenzyl alcohol, 2,3,4,5-tetrafluorobenzyl alcohol, 2,3,4,6-tetrafluorobenzyl alcohol, 2,3,5,6-tetrafluorobenzyl alcohol, 2,4,5,6-tetrafluorobenzyl alcohol, 2,3,4,5,6-pentafluorobenzyl alcohol, 2-(trifluoromethyl)benzyl alcohol, 3-(trifluoromethyl)benzyl alcohol, 4-(trifluoromethyl)benzyl alcohol, 2,3-bis(trifluoromethyl)benzyl alcohol, 2,4-bis(trifluoromethyl)benzyl alcohol, 2,5-bis(trifluoromethyl)benzyl alcohol, 2,6-bis(trifluoromethyl)benzyl alcohol, 3,4-bis(trifluoromethyl)benzyl alcohol, 3,5-bis(trifluoromethyl)benzyl alcohol, 3,6-bis(trifluoromethyl)benzyl alcohol, 2,3,4-tris(trifluoromethyl)benzyl alcohol, 2,3,5-tris(trifluoromethyl)benzyl alcohol, 2,3,6-tris (trifluoromethyl)benzyl alcohol, 2,4,5-tris(trifluoromethyl)benzyl alcohol, 2,4,6-tris(trifluoromethyl)benzyl alcohol, 2,5,6-tris(trifluoromethyl)benzyl alcohol, 3,4,5-tris(trifluoromethyl)benzyl alcohol, 2,3,4,5-tetrakis(trifluoromethyl)benzyl alcohol, 2,3,4,6-tetrakis(trifluoromethyl)benzyl alcohol, 2,3,5,6-tetrakis (trifluoromethyl)benzyl alcohol, 2,4,5,6-tetrakis(trifluoromethyl)benzyl alcohol, 2,3,4,5,6-pentakis(trifluoromethyl) benzyl alcohol, 2-fluoro-3-(trifluoromethyl)benzyl alcohol, 2-fluoro-4-(trifluoromethyl)benzyl alcohol, 2-fluoro-5-(trifluoromethyl)benzyl alcohol, 2-fluoro-6-(trifluoromethyl) benzyl alcohol, 3-fluoro-2-(trifluoromethyl)benzyl alcohol, 3-fluoro-4-(trifluoromethyl)benzyl alcohol, 3-fluoro-5-(trifluoromethyl)benzyl alcohol, 3-fluoro-6-(trifluoromethyl) benzyl alcohol, 4-fluoro-2-(trifluoromethyl)benzyl alcohol, and 4-fluoro-3-(trifluoromethyl)benzyl alcohol.

Of the (meth)acrylate compounds represented by general formula (1), in particular, a fluorine-containing phenoxyalkyl (meth)acrylate compound is which m is 1 to 5 and $R^1$ is an oxyalkylene group is, for example, obtained using a fluorine-containing phenol compound represented by general formula (3) below as a raw material.

[Chemical Formula 4]

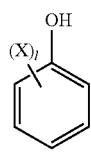

(3)

In general formula (3), each X independently represents a fluorine atom or a methyl group in which at least one hydrogen atom is substituted with a fluorine atom and 1 represents an integer of 1 to 5.

In general formula (3), each of the substituent independently represented by X represents a fluorine atom or a methyl group in which at least one hydrogen atom is substituted with a fluorine atom. Specific examples of the methyl group in which at least one hydrogen atom is substituted with a fluorine atom include a monofluoromethyl group, a difluoromethyl group, and a trifluoromethyl group. Of these groups, the fluorine atom and the trifluoromethyl group are suitable.

In general formula (3), l represents an integer of 1 to 5. X substitutes at any positions of the carbons located at substitutable five positions in the aromatic ring and the bonding position is not limited.

Examples of such fluorine-containing phenol compounds represented by general formula (3) include 2-fluorophenol, 3-fluorophenol, 4-fluorophenol, 2,3-difluorophenol, 2,4-difluorophenol, 2,5-difluorophenol, 2,6-difluorophenol, 3,4-difluorophenol, 3,5-difluorophenol, 3,6-difluorophenol, 2,3,4-trifluorophenol, 2,3,5-trifluorophenol, 2,3,6-trifluorophenol, 2,4,5-trifluorophenol, 2,4,6-trifluorophenol, 2,5,6-trifluorophenol, 3,4,5-trifluorophenol, 2,3,4,5-tetrafluorophenol, 2,3,4,6-tetrafluorophenol, 2,3,5,6-tetrafluorophenol, 2,4,5,6-tetrafluorophenol, 2,3,4,5,6-pentafluorophenol, 2-(trifluoromethyl)phenol, 3-(trifluoromethyl)phenol, 4-(trifluoromethyl)phenol, 2,3-bis(trifluoromethyl)phenol, 2,4-bis(trifluoromethyl)phenol, 2,5-bis(trifluoromethyl)phenol, 2,6-bis(trifluoromethyl)phenol, 3,4-bis(trifluoromethyl)phenol, 3,5-bis(trifluoromethyl)phenol, 3,6-bis(trifluoromethyl) phenol, 2,3,4-tris(trifluoromethyl)phenol, 2,3,5-tris(trifluoromethyl)phenol, 2,3,6-tris(trifluoromethyl)phenol, 2,4,5-tris(trifluoromethyl)phenol, 2,4,6-tris(trifluoromethyl) phenol, 2,5,6-tris(trifluoromethyl)phenol, 3,4,5-tris(trifluoromethyl)phenol, 2,3,4,5-tetrakis(trifluoromethyl) phenol, 2,3,4,6-tetrakis(trifluoromethyl)phenol, 2,3,5,6-tetrakis(trifluoromethyl)phenol, 2,4,5,6-tetrakis(trifluoromethyl)phenol, 2,3,4,5,6-pentakis(trifluoromethyl) phenol, 2-fluoro-3-(trifluoromethyl)phenol, 2-fluoro-4-(trifluoromethyl)phenol, 2-fluoro-5-(trifluoromethyl)phenol, 2-fluoro-6-(trifluoromethyl)phenol, 3-fluoro-2-(trifluoromethyl)phenol, 3-fluoro-4-(trifluoromethyl)phenol, 3-fluoro-5-(trifluoromethyl)phenol, 3-fluoro-6-(trifluoromethyl)phenol, 4-fluoro-2-(trifluoromethyl)phenol, and 4-fluoro-3-(trifluoromethyl)phenol. Of these compounds, in particular, 4-fluorophenol, 3,4-difluorophenol, and 3-(trifluoromethyl) phenol are preferable.

A fluorine-containing phenoxide compound represented by the following general formula (4) below is obtained by reacting the fluorine-containing phenol compound represented general formula (3) with a basic compound.

[Chemical Formula 5]

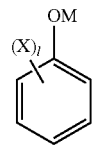

(4)

In general formula (4), M represents an alkali metal atom or an alkaline earth metal atom and 1 represents an integer of 1 to 5.

Examples of the suitable basic compound include inorganic bases such as lithium hydroxide, sodium hydroxide, potassium hydroxide, and calcium hydroxide. Of these compounds, potassium hydroxide is preferable because potassium hydroxide is easily available and inexpensive. Note that these compounds may be used singly or may be used by mixing two or more of the compounds.

A solvent to be used is not particularly limited as long as the solvent has suitable solubility to the raw material and no reactivity to the compound. For example, an alcohol having the same (or similar) carbon number as the carbon number of the alkyl halide alcohols described below can be used.

The reaction temperature of this reaction can be appropriately adjusted by the temperature of the above solvent or the like. It is desirable that the reaction temperature be in the range of 0° C. to 100° C. and preferably in the range of 20° C. to 50° C. from the viewpoints of reaction time and reduction in side reaction.

A fluorine-containing alcohol compound represented by the following general formula (5) below is obtained by reacting the fluorine-containing phenoxide compound represented by general formula (4) serving as a nucleophilic agent with an alkyl halide alcohol.

[Chemical Formula 6]

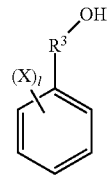

(5)

In general formula (5), $R^3$ represents an oxyalkylene group having a carbon number of 1 to 8, and 1 represents an integer of 1 to 5.

In general formula (5), the oxyalkylene group represented by $R^3$ is preferably a linear or branched oxyalkylene group having a carbon number of 1 to 8. Specific examples of the oxyalkylene group having a carbon number of 1 to 8 include an oxymethylene group, an oxyethylene group, an oxy-n-propylene group, an oxy-isopropylene group, an oxy-n-butylene group, and an oxy-t-butylene group. Of these groups, the oxyethylene group is particularly preferable.

Suitable alkyl halide alcohol is a linear or branched alkyl halide alcohol having a carbon number of 1 to 8 and specific examples of the alkyl halide alcohol include bromomethanol, chloromethanol, iodomethanol, 2-bromoethanol, 2-chloroethanol, 2-iodoethanol, 3-bromo-1-propanol, 3-chloro-1-propanol, 3-iodo-1-propanol, 1-bromo-2-propanol, 1-chloro-2-propanol, 1-iodo-2-propanol, 4-bromo-1-butanol, 4-chloro-1-butanol, 4-iodo-1-butanol, bromo-t-butyl alcohol, chloro-t-butyl alcohol, and iodo-t-butyl alcohol. Of these compounds, 2-bromoethanol is particularly preferable. These compounds may be used singly or may be used by mixing two or more of the compounds.

The reaction temperature of this reaction is desirably in the range of −20° C. to 150° C. and preferably in the range of 60° C. to 110° C. from the viewpoints of reaction time and reduction in side reaction.

A fluorine-containing phenylalkyl (meth)acrylate compound and a fluorine-containing phenoxyalkyl (meth)acrylate compound represented by general formula (1) can be obtained by (meth)acryloylating the fluorine-containing alcohol compound represented by general formulas (2) and (5).

The (meth)acryloylating reaction is carried out by reacting the fluorine-containing alcohol compound with a (meth)acryloylating agent in the presence or absence of a base. Examples of the (meth)acryloylating agent include (meth)acrylic acid chloride and (meth)acrylic anhydride. These agents may be used singly or may be used by mixing two or more of the agents.

The amount of the (meth)acryloylating agent to be used is, for example, about 1.0 molar equivalent to about 2.0 molar equivalents and preferably about 1.0 molar equivalent to about 1.5 molar equivalents relative to the fluorine-containing alcohol compound.

As the base, organic bases are preferable and tertiary amines are particularly suitably used. Specific examples of the base include aliphatic amines such as triethylamine, diisopropylethylamine, N-methylmorpholine, and N-methylpiperidine and aromatic amines such as pyridine. These amines may be used singly or may be used by mixing two or more of the amines.

The amount of the base to be used is, for example, about 1.0 molar equivalent to about 2.0 molar equivalents and preferably about 1.0 molar equivalent to about 1.5 molar equivalents relative to the fluorine-containing alcohol compound.

Although the solvent is not particularly limited, the solvent desirably has no reactivity to the compound. Examples of the solvent include ethers such as THF, diethyl ether, and dimethoxyethane and aromatic hydrocarbons such as benzene, toluene, and xylene.

In addition, other compounds may be added, if necessary. A polymerization inhibitor for preventing polymerization may be added.

Of the (meth)acrylate compounds represented by general formula (1), in particular, examples of a phenylalkyl (meth)acrylate compound in which m is 0 and $R^1$ is an alkylene group include the following compounds.

Examples of the compounds include benzyl (meth)acrylate, phenethyl (meth)acrylate, 3-phenylpropyl (meth)acrylate, 4-phenylbutyl (meth)acrylate, 5-phenylpentyl (math) acrylate, 6-phenylhexyl (meth)acrylate, 7-phenylheptyl (meth)acrylate, and 8-phenyloctyl (meth)acrylate. Of these compounds, benzyl (meth)acrylate is particularly preferable.

Of the (meth)acrylate compounds represented by general formula (1), in particular, examples of a phenoxylalkyl (meth)acrylate compound in which m is 0 and $R^1$ is an oxyalkylene group include the following compounds.

Examples of the compounds include phenoxymethyl (meth)acrylate, 2-phenoxyethyl (meth)acrylate, 3-phenoxypropyl (meth)acrylate, 4-phenoxybutyl (meth)acrylate, 5-phenoxypentyl (meth)acrylate, 6-phenoxyhexyl (meth)acrylate, 7-phenoxyheptyl (meth)acrylate, and 8-phenoxyoctyl (meth)acrylate.

Such a phenylalkyl (meth)acrylate compound and phenoxyalkyl (meth)acrylate compound may be obtained by conventionally known synthetic methods.

Note that the (meth)acrylate compound represented by general formula (1) preferably has a molecular weight of 800 or lower. The molecular weight is more preferably 600 or lower and more preferably 400 or lower.

<(b) Optical Resin Compound>

An optical resin compound to which the additive including the (a) (meth)acrylate compound represented by general formula (1) according to the embodiment of the present invention is added may be a common resin raw material for optical application and is not particularly limited. Examples of the optical resin compound may include resin raw materials including an ABS (acrylonitrile-butadiene-styrene) resin, a PS (polystyrene) resin, a PC (polycarbonate) resin, an AS (acrylonitrile-styrene) resin, a PMMA (polymethyl methacrylate) resin, an EP (epoxy) resin, a phenol (PB) resin, olefin-based resins such as a PE (polyethylene) resin and a PP (polypropylene) resin, and Cytop resin, monomers thereof, and compositions including the monomer.

Of these materials, the optical resin compound that can be used as an optical element on a high dispersion side is effective. Specifically, for example, the optical resin compounds represented by the following general formulas (6) and (7) are exemplified.

[Chemical Formula 7]

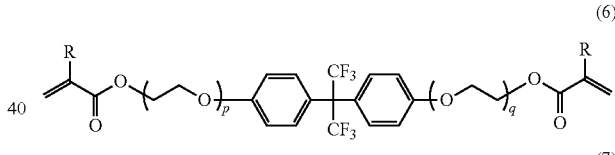

(6)

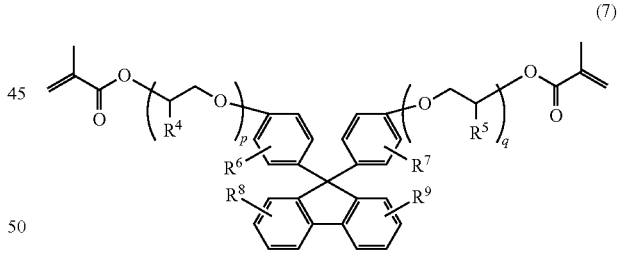

(7)

In general formulas (6) and (7), each R independently represents a hydrogen atom or a methyl group and p and q each are independently an integer of 1 to 3.

In general formula (7), $R^4$ and $R^5$ each are independently a hydrogen atom or an alkyl group having a carbon number of 1 to 2; $R^6$, $R^7$, $R^8$, and $R^9$ each independently represent any one of a hydrogen atom, a fluorine atom, an alkyl group having a carbon number of 1 to 6, or a phenyl group in which some of hydrogen atoms are optionally substituted with an alkyl group having a carbon number of 1 to 6.

<Optical Resin Precursor Composition>

The optical resin precursor composition according to the embodiment of the present invention is obtained by adding the additive including the (a) (meth)acrylate compound represented by general formula (1) according to the embodiment of the present invention to the (b) optical resin compound. Namely, such an optical resin precursor composition is a mixture including the (a) (meth)acrylate compound represented by general formula (1) and the (b) optical resin compound.

<Optical Resin Composition>

The optical resin composition according to the embodiment of the present invention is obtained by polymerizing the additive including the (a) (meth)acrylate compound represented by general formula (1) according to the embodiment of the present invention and the optical resin precursor composition including the (b) optical resin compound. Namely, such an optical resin composition includes a constitutional unit represented by general formula (8).

[Chemical Formula 8]

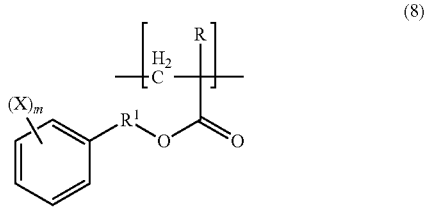

(8)

In general formula (8), each R independently represents a hydrogen atom or a methyl group; each X independently represents a fluorine atom or a methyl group in which at least one hydrogen atom is substituted with a fluorine atom; m represents an integer of 0 to 5; and $R^1$ represents an alkylene group or an oxyalkylene group having a carbon number of 1 to 8.

As an example, the constitutional unit of the copolymer of the compound represented by general formula (1) above and the compound represented by general formula (6) above included in the optical resin composition according to the embodiment of the present invention is illustrated in general formula (9) below.

[Chemical Formula 9]

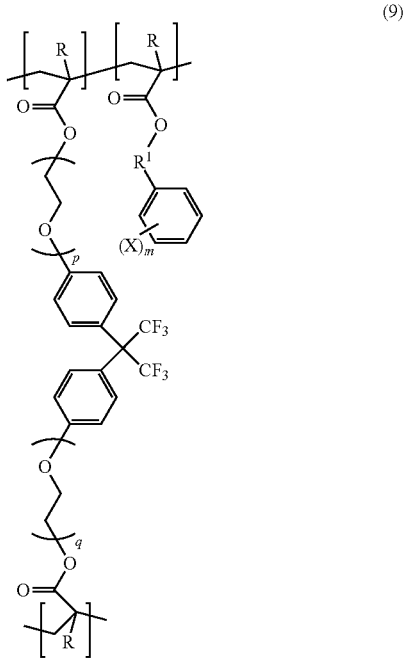

(9)

In general formula (9), each R independently represents a hydrogen atom or a methyl group; p and q each independently represent an integer of 1 to 3; each X independently represents a fluorine atom or a methyl group in which at least one hydrogen atom is substituted with a fluorine atom; m represents an integer of 0 to 5; and $R^1$ represents an alkylene group or an oxyalkylene group having a carbon number of 1 to 8.

A method for polymerizing the copolymer represented by general formula (9) is not particularly limited. A radical polymerization method is preferable from the viewpoint of easy control or the like. Of the types of the radical polymerization, controlled radical polymerization is more preferable. Examples of the controlled radical polymerization method include the chain transfer agent method and a living radical polymerization method, which is a kind of living polymerization. The living radical polymerization is more preferable due to easy control of the molecular weight distribution. Note that examples of the living radical polymerization method include a nitroxy radical polymerization (NMP) method, an atom transfer radical polymerization (ATRP) method, and a reversible addition-fragmentation chain transfer method (RAFT).

<(c) Polymerization Initiator>

Note that, in the case of using the radical polymerization, a conventionally known polymerization initiator may be appropriately used. The polymerization initiator may be used singly or in combination of two or more polymerization initiators. In addition, a commercially available polymerization initiator may be used as is.

Specific examples of the polymerization initiator include alkylphenone-based photopolymerization initiators such as 2,2-dimethoxy-1,2-diphenylethan-1-one, 2-hydroxy-2-methyl-1-phenylpropan-1-one, 2-hydroxy-1-{4-[4-(2-hydroxy-2-methyl-propionyl)-benzyl]phenyl}-2-methyl-propan-1-one, 1-hydroxycyclohexyl phenyl ketone, 1-[4-(2-hydroxyethoxy)-phenyl]-2-hydroxy-2-methyl-1-propan-1-one, and 2-methyl-1-[4-(methylthio)phenyl]-2-morpholinopropan-1-one, and acyl phoshine oxide-based photopolymerization initiators such as phenyl-bis(2,4,6-trimethylbenzoyl)phosphine oxide and 2,4,6-trimethylbenzoyldiphenylphosphine oxide. Of these compounds, 1-hydroxycyclohexyl phenyl ketone is particularly preferable.

The other additives may be appropriately used. For example, a refractive index adjusting component that can reduce fluctuation in the refractive index due to the production process of the raw material and adjust the refractive index of the resin precursor mixture after curing to a desired value can be appropriately added. This allows the diffraction properties of the diffractive optical element to be stabilized. As the refractive index adjusting component, a component exhibiting an effect by adding a small amount of the component is preferable and a compound having a lower refractive index than that of the main component is further preferable. Example of the refractive index adjusting component include 2,2,2-trifluoroethyl (meth)acrylate and 1,6-bis(acryloyloxy)-2,2,3,3,4,4,5,5-octafluorohexane (hereinafter referred to as Compound A). The refractive index adjusting component, however, is not limited to the above compounds.

A catalyst used in the polymerization reaction can be appropriately used depending on the polymerization method. In addition, a ligand in accordance with the metal catalyst can be appropriately used.

Other common additives may be further added in order to impart properties such as adhesiveness, coating uniformity, chemical resistance, and heat resistance.

The copolymer obtained by the living radical polymerization method can be subjected to further chemical reaction to convert the functional groups. The optical resin composition according to the embodiment of the present invention shall also include the copolymer after such a conversion. Examples of the conversion of the functional groups include esterification of a carboxy group originated from (meth)acrylate.

Moreover, the optical resin precursor composition according the embodiment of the present invention may include two or more of the (meth)acrylate compounds containing at least one constitutional unit represented by general formula (1). The optical resin precursor composition may also include one or more of any other constitutional units.

Thus prepared optical resin precursor composition has excellent moldability.

In general, the optical resin precursor composition having a low refractive index and high dispersion has been known for high viscosity. Molding of the optical resin precursor composition having high viscosity using a mold causes a problem of mixing bubbles into the cured product. Preparation of the optical resin precursor composition by mixing the above-described additive to the optical resin precursor composition at a predetermined ratio allows the viscosity of the composition to be suitable for molding. The range of the viscosity suitable for the molding using a mold is different depending on the molding process to be applied and is approximately 500 MPa·s to 5,000 MPa·s.

Thus synthesized copolymer having a constitutional unit represented by general formula (8) also has excellent transparency and thermal properties. In general, high transparency is required for the optical resin composition and thus the optical resin composition desirably has an internal transmittance of 95% or higher in the entire wavelength range of 400 nm to 800 nm at a thickness of 100 nm. The resin composition obtained by curing the above-described optical resin precursor composition has an internal transmittance of 96% or higher (98.0% or higher in the wavelength range of 430 nm to 650 nm) over the entire wavelength range of 400 nm to 800 nm at a thickness of 100 nm and thus satisfies the condition of the internal transmittance.

The types of lens obtained by forming a contact multilayer diffractive optical element include a bonding type in which the contact multilayer diffractive optical element is sandwiched between two lenses and a non-bonding type in which the contact multilayer diffractive optical element is formed on one side of one lens and no lens is bonded on the diffractive optical element. These two types have the same function of the diffractive optical element. The non-bonding type, however, requires one glass lens less than the bonding type and thus is particularly advantageous in an optical system for which reduction in size and weight is required. The non-bonding molding type diffractive optical element allows the diffractive optical component having a spherical or aspherical surface shape to be molded by transferring the lens shape in the mold to a resin surface at the time of molding the diffractive optical component. In this case, the resin surface shape after molding may be different from the reverse shape of the mold due to cure shrinkage of the resin. In that case, the shape can be corrected by the correction processing of the mold shape so that the molded surface of the resin can be molded in the desired shape. In some cases, the shape can be corrected by polishing the uppermost surface of the diffractive optical element, and thus the shape of the outermost surface can be selected freely while a highly precise resin surface can be molded.

On the other hand, the resin molding face of the non-bonding type is in contact with the air and thus an antireflection coating is required to be formed on the uppermost surface of the diffractive optical element to reduce the surface reflection. However, a large difference in linear expansion coefficient between materials is likely to cause crack generation in the coating when the antireflection coating made of an inorganic material is applied onto the diffractive optical element made of a resin material. The resin material having low storage elastic modulus causes deformation of the resin layer due to the compressive stress of the antireflection coating layer when the resin is heated in the process of antireflection coating or the like. This deformation causes a problem of generating fine wrinkles on the surface after coating. It has been known that these cracks and wrinkles are also similarly generated when a diffractive optical element layer made of a different material is further laminated onto the diffractive optical element layer made of the resin material and the thermal properties of the diffractive optical element layer serving as the underlayer affect the antireflection coating serving as the uppermost layer. In general, when the resin having a large linear expansion coefficient is molded on a glass lens, the resin is expanded or shrined by environmental temperature change. This results in changing the surface shape of the integrated glass lens.

From these viewpoints, the optical resin composition after curing desirably satisfies the predetermined conditions of the linear expansion coefficient and a storage elastic modulus. For example, a linear expansion coefficient of the material constituting the diffractive optical element is preferably $2.0 \times 10^{-4}$ (1/K, 25° C. to 70° C.) or lower. Moreover, in the case where the diffractive optical component forms a lens shape and has a resin thickness difference of 1,000 μm or larger, the linear expansion coefficient is preferably $1.2 \times 10^{-4}$ (1/K, 25° C. to 70° C.) or lower. The storage elastic modulus at 100° C. is preferably 19 MPa or higher. The above-described optical resin composition satisfies these thermal properties.

Conventionally, to satisfy both diffractive optical properties and thermal properties has been considered to be difficult. The optical resin composition made by curing the above-described optical resin precursor composition, however, allows the optical resin composition satisfying both diffractive optical properties and thermal properties to be obtained.

<Diffractive Optical Element>

Such an optical resin precursor composition according to the embodiment of the present invention is suitable as, for example, a diffractive optical element provided in a number of optical devices. Hereinafter, the optical element and the optical device used in the embodiment of the present invention will be described.

FIG. 1 illustrates an example of a structure (sectional shape) of a common contact multilayer diffractive optical element (DOE). This diffractive optical element is configured of a first diffractive optical component 1 made of a resin having a low refractive index and high dispersion and a second diffractive optical component 2 made of a resin having a high refractive index and low dispersion. A sawtooth relief pattern 5 (diffraction grating pattern) is formed between both diffractive optical components.

FIGS. 2A to 2I illustrate seven additional structural examples of the contact multilayer diffractive optical elements (DOE). The contact multilayer diffractive optical element (DOE) is formed by stacking a resin having a high refractive index and low dispersion and a resin having a low refractive index and high dispersion compared with the first resin and is what is called a contact multilayer optical element in which a diffraction grating is located at the interface. The contact multilayer optical element may be formed on a single substrate or may have a configuration in which the optical element is sandwiched between two substrates. The substrate(s) may be a parallel flat plate or may be a plano-concave shape, plano-convex shape, a meniscus shape, or a biconvex shape. The contact multilayer optical element may be formed on a plane or may be formed on a convex surface or on a concave surface. Either of the high refractive index and low dispersion resin or the low refractive index and high dispersion resin may be formed as the first layer. An antireflection may be formed on the upper surface of the contact multilayer optical element formed on a single substrate.

The convex surface and concave surface of the substrate may be an aspherical surface. The surface of the air layer side of the second layer of optical element formed on a single substrate may be an aspherical surface.

The optical component and optical element according to the embodiment of the present invention are widely used for, for example, an image-taking optical system, a microscope optical system, and an observation optical system. An appropriately optimal configuration can be selected depending on the application and the form of the optical system.

Figure 3:
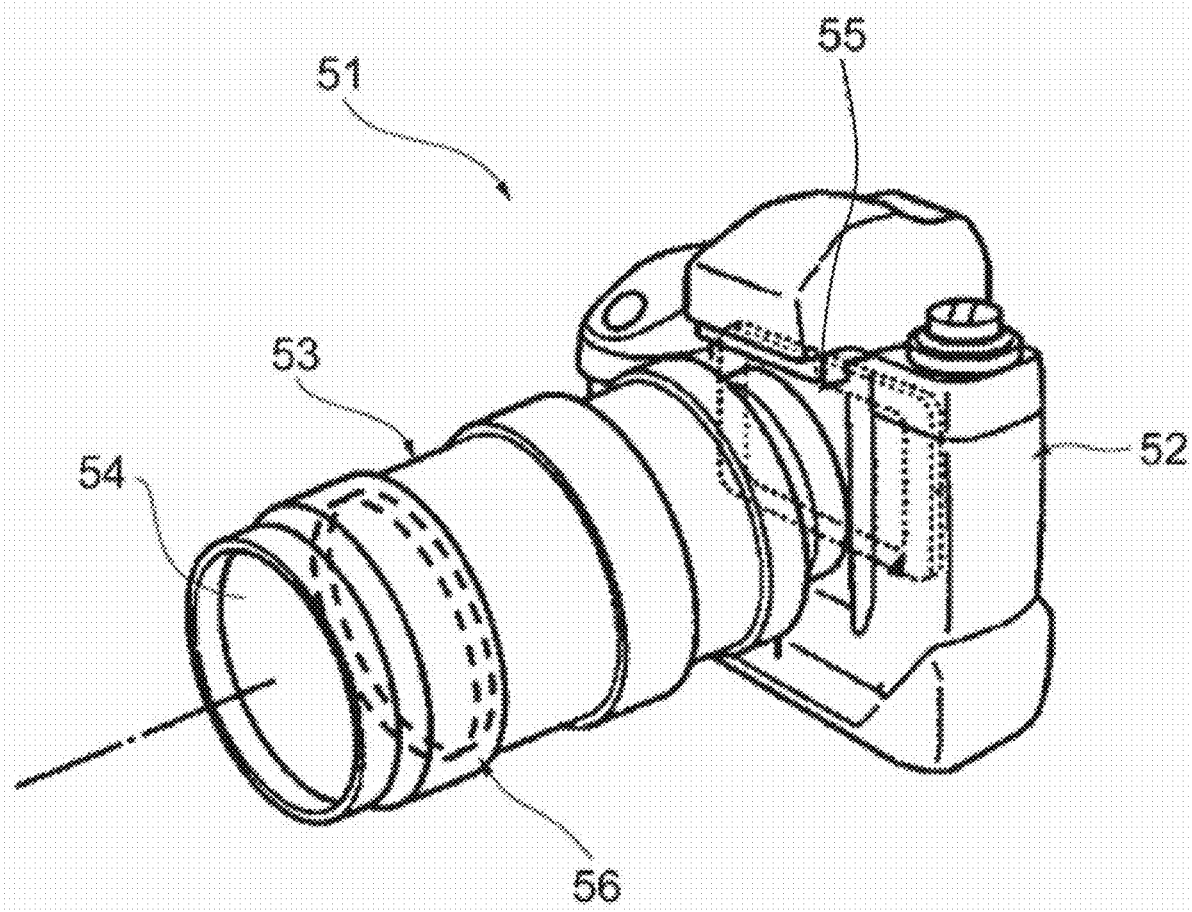
FIG. 3 is an explanatory view of an image-taking device equipped with the contact multilayer diffractive optical element (DOE) in which an optical resin precursor composition according to an embodiment of the present invention serves as a base material.

As an example of the optical device, FIG. 3 illustrates an image-taking device 51 mounting a contact multilayer diffractive optical element (DOE) using the optical resin composition according to the embodiment of the present invention as a base material.

The image-taking device 51 is what is called a digital single-lens reflex camera and a lens barrel 53 is removably attached to a lens mount (not illustrated) of a camera body 52. The light passed through the image-taking lens 54 in the lens barrel 53 is imaged on a multi-chip module sensor chip (solid-state image-taking element) 55 located on the rear side of the camera body 52. At least one lens group 56 constituting the image-taking lens 54 includes the above-described contact multilayer diffractive optical element (DOE).

Note that the optical device is not limited to such an image-taking device and examples of the optical device include microscopes, binoculars, telescopes, security cameras, and projectors.

EXAMPLE

Hereinafter, the embodiment of the present invention will be described more specifically with reference to Examples and Comparative Examples. However, the embodiment of the present invention is not limited by these Examples.

[Synthesis of (meth)acrylate Compounds]

(Meth)acrylate compounds were synthesized by the methods described below.

Example 1

Synthesis of EA2

Into a flask, 5.40 g (96.3 mmol) of potassium hydroxide, 100 mL of ethanol, and 12.5 g (96.3 mmol) of 3,4-difluorophenol (manufactured by Tokyo Chemical Industry Co., Ltd.) were charged, and the resultant mixture was sufficiently stirred at 25° C. Thereafter, ethanol serving as the solvent and water generated as a by-product were distilled off under reduced pressure to prepare potassium 3,4-difluorophenoxide.

Thereafter, 15.1 g (121 mmol) of 2-bromoethanol (manufactured by Tokyo Chemical Industry Co., Ltd.) was added and the resultant mixture was heated and stirred at 90° C. for 24 hours. After completion of the reaction, the precipitated salt was removed and the obtained liquid was transferred to a separatory funnel. Dichloromethane was added into the separatory funnel and the organic phase was washed with a potassium hydroxide aqueous solution, a saturated sodium hydrogen carbonate aqueous solution, and a saturated brine. The organic phase was transferred to a flask and dried over sodium sulfate. Thereafter, the dried organic phase was concentrated under reduced pressure to give 12.4 g of a crude product. The crude product was purified by column chromatography using silica gel serving as a column packing and a mixed solvent of hexane-acetone serving as a developing solvent to give 10.1 g (57.7 mmol) of 2-(3,4-difluorophenoxy)ethanol as a yellow transparent liquid.

The measurement results by $^1$H-NMR (NM-ECA400, manufactured by JEOL Ltd.) are listed below. Here, a signal of Si—$CH_3$ protons of tetramethylsilane serving as a reference substance was used as a reference ($\delta$=0 ppm).

$^1$H-NMR (400 MHz, TMS): $\delta$=1.98 (1H, s, —OH), 5.99 (4H, m, —$CH_2$—$CH_2$—), 6.62 (1H, m, Ph-H), 6.72 (1H, m, Ph-H), 7.07 (1H, q, Ph-H)

Into a flask, 10.1 g (57.7 mmol) of obtained 2-(3,4-difluorophenoxy)ethanol, 5.83 g (57.7 mmol) of triethylamine, and 30 mL of tetrahydrofuran were charged. The flask was cooled with ice and 6.79 g (75.0 mmol) of acryloyl chloride (manufactured by Tokyo Chemical Industry Co., Ltd.) was added dropwise with stirring and the resultant mixture was stirred at room temperature for 1 hour after completion of the addition. White precipitate was removed and the resultant liquid was concentrated under reduced pressure. Thereafter, dichloromethane was added to the concentrated liquid and the resultant liquid was transferred to a separatory funnel. The organic phase was washed with a sodium hydrogen carbonate saturated aqueous solution and a saturated brine and dried over sodium sulfate. Thereafter, the dried liquid was concentrated under reduced pressure to give 6.96 g of a crude product (a pale yellow transparent liquid). The crude product was purified by column chromatography using silica gel serving as a column packing and a mixed solvent of hexane-acetone serving as a developing solvent to give, as colorless transparent liquid, 5.15 g (22.6 mmol) of 2-(3,4-difluorophenoxy)ethyl acrylate represented by general formula (10) below.

$^1$H-NMR (400 MHz, TMS): $\delta$=4.16 (2H, m, —$CH_2$—), 4.50 (2H, m, —$CH_2$—), 5.88 (1H, m, —CH=$CH_2$), 6.16 (1H, q, —CH=$CH_2$), 6.45 (1H, q, —CH=$CH_2$), 6.62 (1H, m, Ph-H), 6.75 (1H, m, Ph-H), 7.07 (1H, q, Ph-H)

Example 2

Synthesis of EA1

The same (or similar) process was carried out using 4-fluorophenol instead of 3,4-difluorophenol in Example 1 above to give 2-(4-fluorophenoxy) ethyl acrylate represented by the following general formula (11).

$^1$H-NMR (400 MHz, TMS): $\delta$=4.30 (2H, m, —$CH_2$—), 4.53 (2H, m, —$CH_2$—), 5.86 (1H, dd, —CH=$CH_2$), 6.16 (1H, dd, —CH=$CH_2$), 6.44 (1H, dd, —CH=$CH_2$), 6.90-7.12 (4H, m, Ph-H)

Example 3

Synthesis of EA3

The same (or similar) process was carried out using 3,4,5-trifluorophenol instead of 3,4-difluorophenol in Example 1 above to give 2-(3,4,5-trifluorophenoxy)ethyl acrylate represented by the following general formula (12).

$^1$H-NMR (400 MHz, TMS): δ=4.14 (2H, m, —CH$_2$—), 4.49 (2H, m, —CH$_2$—), 5.89 (1H, dd, —CH=CH$_2$), 6.16 (1H, dd, —CH=CH$_2$), 6.46 (1H, dd, —CH=CH$_2$), 6.54 (28, m, Ph-H)

Example 4

Synthesis of EA4

The same (or similar) process was carried out using 2,3,5,6-tetrafluorophenol instead of 3,4-difluorophenol in Example 1 above to give 2-(2,3,5,6-tetrafluorophenoxy)ethyl acrylate represented by the following general formula (13).

$^1$H-NMR (400 MHz, TMS): δ=4.48 (4H, m, —CH$_2$—CH$_2$—), 5.88 (1H, dd, —CH=CH$_2$), 6.14 (1H, dd, —CH=CH$_2$), 6.42 (1H, dd, —CH=CH), 6.80 (1H, m, Ph-H)

Example 5

Synthesis of EA5

The same (or similar) process was carried out using 2,3,4,5,6-pentafluorophenol instead of 3,4-difluorophenol in Example 1 to give 2-(perfluorophenoxy) ethyl acrylate represented by the following general formula (14).

$^1$H-NMR (400 MHz, TMS): δ=4.40 (2H, t, —CH$_2$—), 4.49 (2H, t, —CH$_2$—), 5.88 (1H, —CH=CH$_2$), 6.13 (1H, dd, —CH=CH$_2$), 6.43 (1H, dd, —CH=CH$_2$)

Example 6

Synthesis of EM2

The same (or similar) process was carried out using methacryloyl chloride instead of acryloyl chloride in Example 1 above to give 2-(3,4-difluorophenoxy)ethyl methacrylate represented by the following general formula (15).

$^1$H-NMR (400 MHz, TMS): δ=1.95 (3H, s, —CH$_3$), 4.17 (2H, t, —CH$_2$—), 4.48 (2H, t, —CH$_2$—), 5.60 (1H, quin, =CH$_2$), 6.14 (1H, s, =CH$_2$), 6.62 (1H, m, Ph-H), 6.75 (1H, m, Ph-H), 7.07 (1H, q, Ph-H)

Example 7

Synthesis of EM1

The same (or similar) process was carried out using methacryloyl chloride instead of acryloyl chloride in Example 2 above to give 2-(4-fluorophenoxy)ethyl methacrylate represented by the following general formula (16).

$^1$H-NMR (400 MHz, TMS): δ=1.95 (3H, t, —CH$_3$), 4.31 (2H, m, —CH$_2$—), 4.51 (2H, m, —CH$_2$—), 5.59 (1H, m, =CH$_2$), 6.14 (1H, s, =CH$_2$), 6.44 (1H, dd, —CH=CH$_2$), 6.90-7.12 (4H, m, Ph-H)

Example 8

Synthesis of EM3

The same (or similar) process was carried out using 3-trifluoromethylphenol instead of 3,4-difluorophenol and methacryloyl chloride instead of acryloyl chloride in Example 1 above to give 2-(3-trifluoromethylphenoxy)ethyl methacrylate represented by the following general formula (17).

$^1$H-NMR (400 MHz, TMS): δ=1.95 (3H, s, —CH$_3$), 4.27 (2H, t, CH$_2$—), 4.52 (2H, t, —CH$_2$—), 5.60 (1H, q, =CH$_2$), 6.14 (1H, q, =CH$_2$), 7.09 (1H, dd, Ph-H), 7.16 (1H, t, Ph-H), 7.23 (1H, d, 7.40 (1H, t, Ph-H)

[Chemical Formula 10]

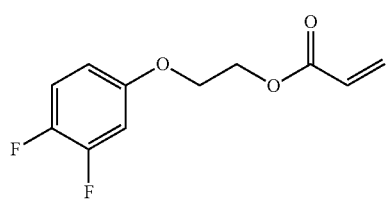

(10)

BA2

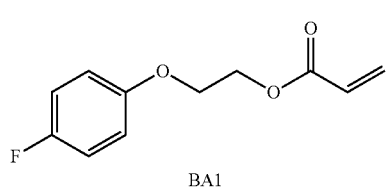

(11)

BA1

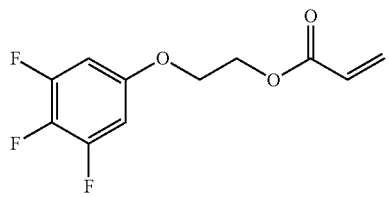

(12)

BA3

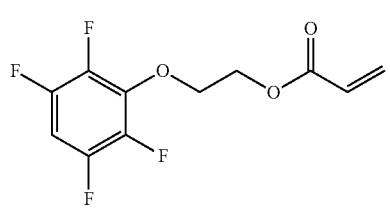

(13)

BA4

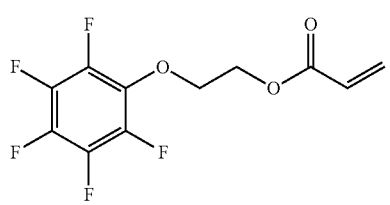

(14)

BA5

-continued

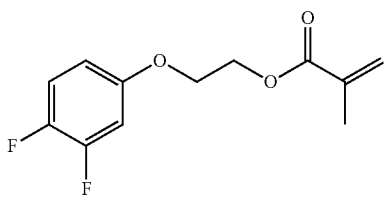

BM2 (15)

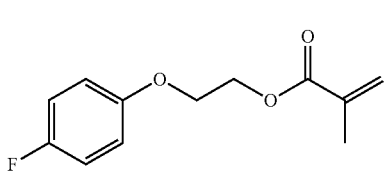

BM1 (16)

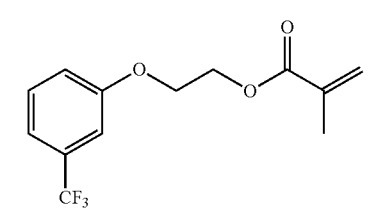

BM3 (17)

Example 9

Synthesis of BA3

Into a flask, 6.5 g (40 mmol) of 2,4,5-trifluorobenzyl alcohol, 4.0 g (40 mmol) of triethylamine, and 20 mL of dichloromethane were charged. The flask was cooled with ice and 4.0 g (44 mmol) of an acryloyl chloride (manufactured by Tokyo Chemical Industry Co., Ltd.) solution diluted with 10 mL of dichloromethane was added dropwise with stirring. After completion of the addition, the resultant solution was continuously stirred at room temperature for 1 hour. White precipitate was removed and the resultant liquid was transferred to a separatory funnel. The organic phase was washed with hydrochloric acid (5 mM), a saturated sodium hydrogen carbonate aqueous solution, and a saturated brine and dried over sodium sulfate. Thereafter, the dried liquid was concentrated under reduced pressure to give 6.9 g of a crude product (pale yellow transparent liquid). The crude product was purified by column chromatography using silica gel serving as a column packing and a mixed solvent of hexane/dichloromethane=1/1 (vol/vol) serving as a developing solvent to give, as colorless transparent liquid, 4.7 g (21 mmol) of 2,4,5-trifluorobenzyl acrylate represented by general formula (18) below.

$^1$H-NMR (400 MHz, TMS): δ=5.20 (2H, s, —CH$_2$—), 5.90 (1H, dd, —CH=CH$_2$), 6.16 (1H, q, —CH=CH$_2$), 6.47 (1H, dd, —CH=CH$_2$), 6.96 (1H, m, Ph-H), 7.26 (1H, m, Ph-H)

Example 10

Synthesis of BA4

The same (or similar) process was carried out using 2,3,4,5-tetrafluorobenzyl alcohol instead of 2,4,5-trifluorobenzyl alcohol in Example 9 above to give 2,3,4,5-tetrafluorobenzyl acrylate represented by the following general formula (19).

$^1$H-NMR (400 MHz, TMS): δ=5.22 (2H, s, —CH$_2$—), 5.92 (1H, dd, —CH=CH$_2$), 6.16 (1H, q, —CH=CH$_2$), 6.48 (1H, dd, —CH=CH$_2$), 7.07 (1H, m, Ph-H)

Example 11

Synthesis of BA5

The same (or similar) process was carried out using pentafluorobenzyl alcohol instead of 2,4,5-trifluorobenzyl alcohol in Example 9 to give perfluorobenzyl acrylate represented by the following general formula (20).

$^1$H-NMR (400 MHz, TMS): δ=5.29 (2H, s, —CH$_2$—), 5.89 (1H, dd, —CH=CH$_2$), 6.12 (1H, q, —CH=CH$_2$), 6.45 (1H, dd, —CH=CH$_2$)

[Chemical Formula 11]

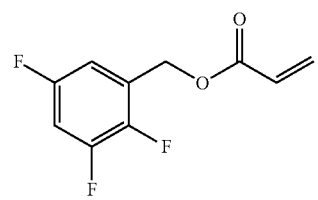

BA3 (18)

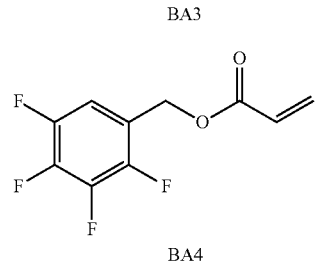

BA4 (19)

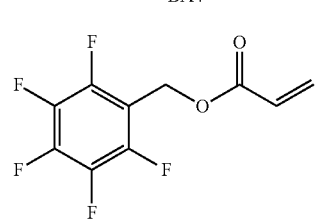

BA5 (20)

[Preparation of Optical Resin Precursor Composition]

The optical resin precursor compositions were prepared by the method described below.

Example 12

Preparation of Resin Precursor of BAHF and EA2 (BAHF-EA2)

Ten parts by mass of 2-(3,4-difluorophenoxy)ethyl acrylate (EA2) obtained in Example 1 above and 90 parts by mass of 2,2-bis((acryloyloxy)ethoxy)phenyl-1,1,1,3,3,3-hexafluoropropane (BAHF) represented by the following general formula (21) were mixed and the resultant mixture was stirred at 23° C. until the mixture became homogeneous. Here, BAHF was synthesized by the conventionally known synthetic method (Chemical Papers, 2014, vol. 68, #11, pp. 1561-1572).

[Chemical Formula 12]

(21)

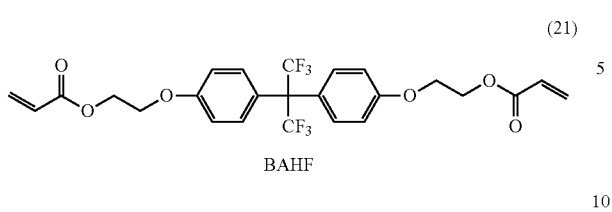

BAHF

To 100 parts by mass of this mixture, 0.5 part by mass of 1-hydroxy cyclohexyl phenyl ketone (hereinafter referred to as HCPK) (Irgacure 184; manufactured by BASF Japan Ltd.) as a photopolymerization initiator was added (BAHF:EA2:HCPK=90:10:0.5) to prepare an optical resin precursor composition. After photocuring, this composition includes the constitutional unit represented by the following general formula (22). Moreover, the compositions having composition ratios of BAHF:EA2=80:20 parts by mass and 70:30 parts by mass were similarly processed to prepare optical resin precursor compositions having individual ratios.

Example 13

Preparation of Resin Precursor Composition of BAHF and EA1 (BAHF-EA1)

The same (or similar) process was carried out using 2-(4-fluorophenoxy)ethyl acrylate (EA1) obtained in Example 2 above instead of EA2 in Example 12 above to prepare an optical resin precursor composition (BAHF:EA1:HCPK=90:10:0.5). After photocuring, this composition includes the constitutional unit represented by the following general formula (23).

[Chemical Formula 13]

(22)

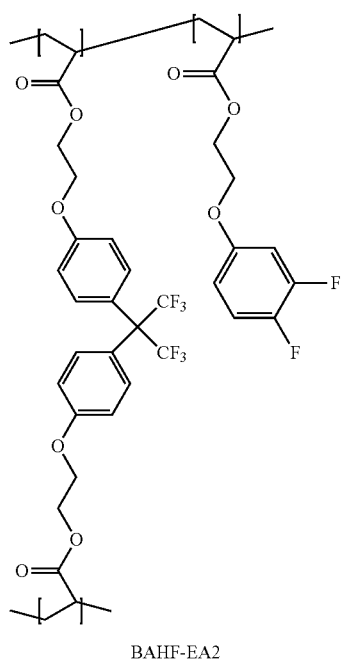

BAHF-EA2

(23)

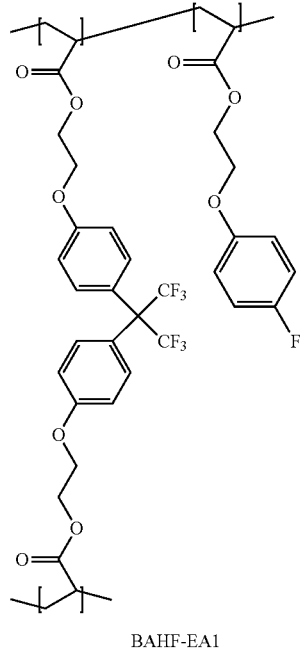

BAHF-EA1

Example 14

Preparation of Resin Precursor Composition of BAHF and EA3 (BAHF-EA3)

The same (or similar) process was carried out using 2-(3,4,5-trifluorophenoxy)ethyl acrylate (EA3) obtained in Example 3 above instead of EA2 in Example 12 above to prepare an optical resin precursor composition (BAHF:EA3:HCPK=90:10:0.5). After photocuring, this composition includes the constitutional unit represented by the following general formula (24).

Example 15

Preparation of Resin Precursor Composition of BAHF and EA4 (BAHF-EA4)

The same (or similar) process was carried out using 2-(2,3,5,6-tetrafluorophenoxy)ethyl acrylate (EA4) obtained in Example 4 above instead of EA2 in Example 12 above to prepare an optical resin precursor composition (BAHF:EA4:HCPK=90:10:0.5). After photocuring, this composition includes the constitutional unit represented by the following general formula (25).

[Chemical Formula 14]

(24)

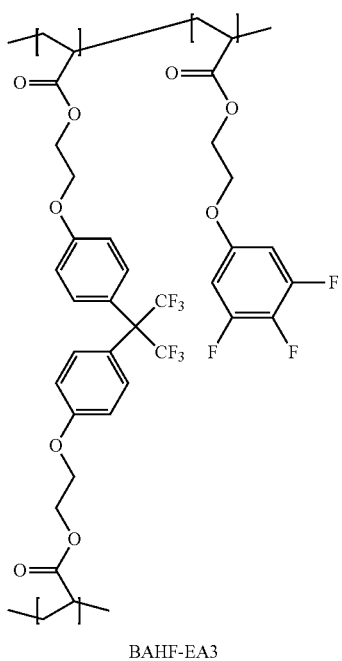

BAHF-EA3

Example 16

Preparation of Resin Precursor Composition of BAHF and EA5 (BAHF-EA5)

The same (or similar) process was carried out using 2-(perfluorophenoxy)ethyl acrylate (EA5) obtained in Example 5 above instead of EA2 in Example 12 above to prepare an optical resin precursor composition (BAHF:EA5:HCPK=90:10:0.5). After photocuring, this composition includes the constitutional unit represented by the following general formula (26).

Example 17

Preparation of Resin Precursor Composition of BAHF and EM2 (BAHF-EM2)

The same (or similar) process was carried out using 2-(3,4-difluorophenoxy)ethyl methacrylate (EM2) obtained in Example 6 above instead of EA2 in Example 12 above to prepare as optical resin precursor composition (BAHF:EM2:HCPK=90:10:0.5). After photocuring, this composition includes the constitutional unit represented by the following general formula (27). Moreover, the composition having a composition ratio of BAHF:EM2:HCPK=80:20:0.5 parts by mass was similarly processed to prepare an optical resin precursor composition.

[Chemical Formula 15]

(25)

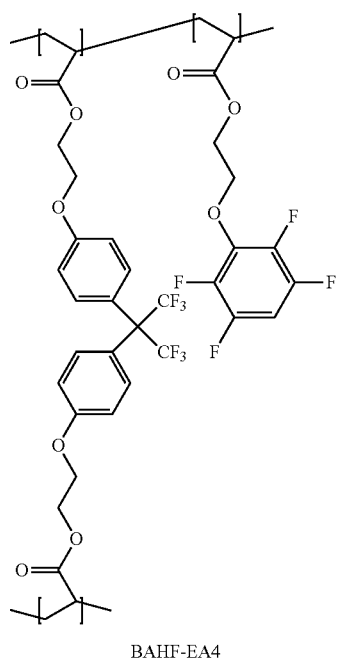

BAHF-EA4

(26)

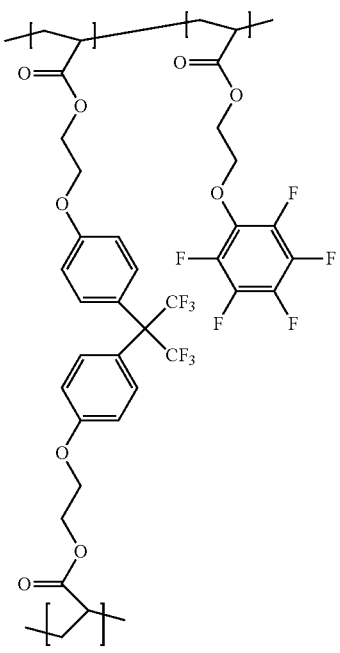

BABF-EA5

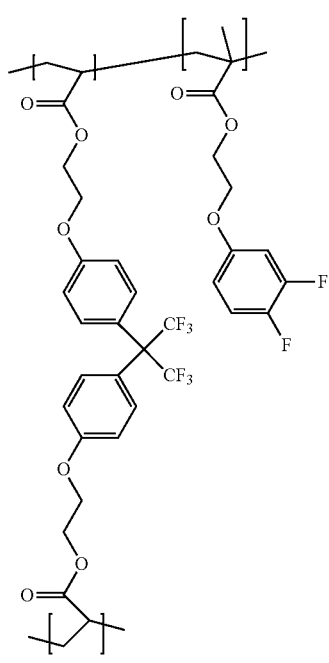

BABF-EM2

Example 18

Preparation of Resin Precursor Composition of BAHF and EM1 (BAHF-EM1)

The same (or similar) process was carried out using 2-(4-fluorophenoxy)ethyl methacrylate (EM1) obtained in Example 7 above instead of EA2 in Example 12 above to prepare an optical resin precursor composition (BAHF:EM1:HCPK=90:10:0.5). After photocuring, this composition includes the constitutional unit represented by the following general formula (28).

Example 19

Preparation of Resin Precursor Composition of BAHF and EA3 (BAHF-EA3)

The same (or similar) process was carried out using 2-(3-trifluoromethylphenoxy)ethyl methacrylate (au) obtained in Example 8 above instead of EA2 in Example 12 above to prepare an optical resin precursor composition (BAHF:EM3:HCPK=90:10:0.5). After photocuring, this composition includes the constitutional unit represented by the following general formula (29).

[Chemical Formula 16]

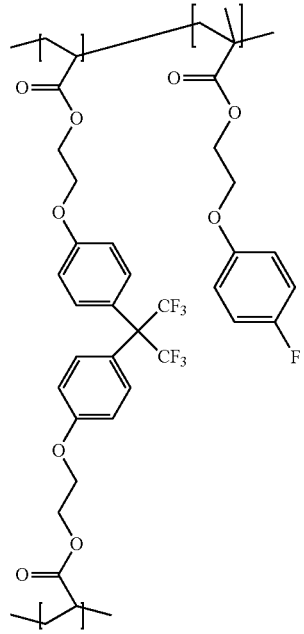

BAHF-EM1

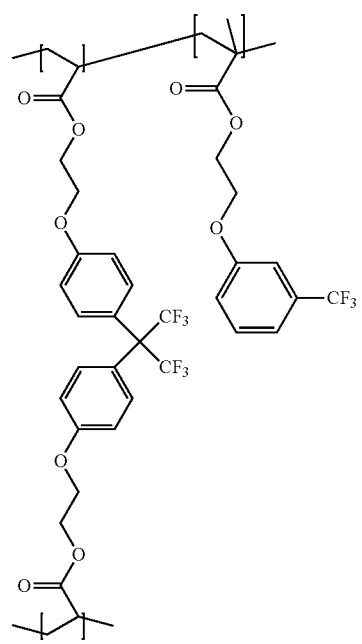

BAHF-EM2

Example 20

Preparation of Resin Precursor Composition of BAHF and EA0 (BAHF-EA0)

The same (or similar) process was carried out using known 2-phenoxyethyl acrylate (EA0) (Shin-Nakamura Chemical Co., Ltd.) represented by the following general formula (30) instead of EA2 in Example 12 above to prepare an optical resin precursor composition (BAHF:EA0:

HCPK=90:10:0.5). After photocuring, this composition includes the constitutional unit represented by the following general formula (32).

Example 21

Preparation of Resin Precursor Composition of BAHF and EM0 (BAHF-EM0)

The same (or similar) process was carried out using known 2-phenoxyethyl methacrylate (EM0) (Shin-Nakamura Chemical Co., Ltd.) represented by the following general formula (31) instead of 2-(3,4-difluorophenoxy) ethyl methacrylate (EA2) obtained in Example 1 above to prepare an optical resin precursor composition (BAHF: EM0:HCPK=90:10:0.5). After photocuring, this composition includes the constitutional unit represented by the following general formula (33).

[Chemical Formula 17]

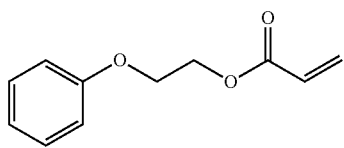

EA0 (30)

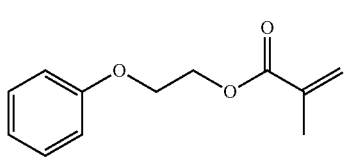

EM0 (31)

[Chemical Formula 18]

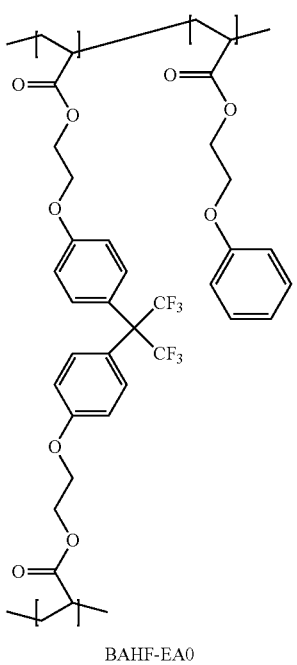

BAHF-EA0 (32)

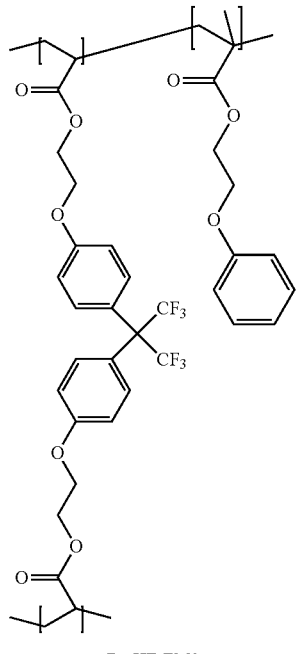

BAHF-EM0 (33)

Example 22

Preparation of Resin Precursor Composition of BAHF and EA2 (BAHF-EA2-Compound A)

The same (or similar) process as the process in Example 12 above was carried out by adding 1,6-bis(acryloyloxy)-2,2,3,3,4,4,5,5-octafluorohexane (Compound A) as a refractive index adjusting component to prepare an optical resin precursor composition (BAHF:EA0:Compound A:HCPK= 85:12:3:0.5). Moreover, the compositions having composition ratios of BAHF:EM2:Compound A=85:12:3 parts by mass and 80:17:3 parts by mass were similarly processed to prepare optical resin precursor compositions in individual ratios.

Example 23

Preparation of Resin Precursor Composition of BAHF and EM0 (BAHF-EM0-Compound A)

The same (or similar) process as the process in Example 20 above was carried out by adding 1,6-bis(acryloyloxy)-2,2,3,3,4,4,5,5-octafluorohexane (Compound A) as a refractive index adjusting component to prepare an optical resin precursor composition (BAHF:EM0:Compound A:HCPK= 85:12:3:0.5). Moreover, the composition having a composition ratio of BAHF:EM0:Compound A=85:12:3 parts by mass was similarly processed to prepare an optical resin precursor composition.

Example 24

Preparation of Resin Precursor Composition of BAHF and EM0 (BAHF-EM0-Compound A)

The same (or similar) process as the process in Example 21 above was carried out by adding 1,6-bis(acryloyloxy)-2, 2,3,3,4,4,5,5-octafluorohexane (Compound A) as a refractive index adjusting component to prepare an optical resin precursor composition (BAHF:EM0:Compound A:HCPK= 85:12:3:0.5). Moreover, the composition having a composition ratio of BAHF:EM0:Compound A=85:12:3 parts by mass was similarly processed to prepare an optical resin precursor composition.

Comparative Example 1

BAHF Resin Precursor Composition

The composition having a composition ratio of BAHF: HCPK=100:0.5 without adding EA2 was similarly processed to prepare a BAHF optical resin precursor composition (BAHF).
<Viscosity Measurement of Optical Resin Precursor Composition>
[Evaluation]
Evaluation was made for the optical resin precursor compositions of Examples 12, 14 to 17, and 20 to 24 and Comparative Example 1 before curing,
The viscosities of the resin precursor compositions prepared in Examples 12, 14 to 17, and 20 to 24 and Comparative Example 1 above were measured at 25° C. using a viscometer (TVE-35H, manufactured by Toki Sangyo Co., Ltd.). The results of these viscosity measurements are listed in Table 1 below.

TABLE 1

| | Composition ratio | | Viscosity (mPa · s) |
|---|---|---|---|
| Example 12 | BAHF:EA2:HCPK | 90:10:0.5 | 4,110 |
| | | 80:20:0.5 | (1,130) |
| | | 70:30:0.5 | (400) |
| Example 14 | BAHF:EA3:HCPK | 90:10:0.5 | 4,680 |
| Example 15 | BAHF:EA4:HCPK | 90:10:0.5 | 4,150 |
| Example 16 | BAHF:EA5:HCPK | 90:10:0.5 | 4,280 |
| Example 17 | BAHF:EM2:HCPK | 90:10:0.5 | (3,770) |
| | | 80:20:0.5 | (1,290) |
| Example 20 | BAHF:EA0:HCPK | 90:10:0.5 | 3,360 |
| Example 21 | BAHF:EM0:HCPK | 90:10:0.5 | 3,560 |
| Example 22 | BAHF:EA2:Compound A:HCPK | 90:7:3:0.5 | (4,490) |
| | | 85:12:3:0.5 | (2,160) |
| | | 80:17:3:0.5 | (1,240) |
| Example 23 | BAHF:EA0:Compound A:HCPK | 90:7:3:0.5 | (4,040) |
| | | 85:12:3:0.5 | (1,910) |
| Example 24 | BAHF:EM0:Compound A:HCPK | 90:7:3:0.5 | (4,000) |
| | | 85:12:3:0.5 | (1,960) |
| Comparative Example 1 | BAHF:HCPK | 100:0.5 | 19,800 (16,500) |

Note that the viscosities of BAHF are different depending on the lots.
The numeric values in ( ) represent measurement results of BAHF Lot 1: mixture having a viscosity of 16,500 mPa·s, whereas the numeric values without ( ) represent measurement results of BAHF Lot 2: mixture having a viscosity of 19,800 mPa·s.
From the above results, it was found that the viscosities of the mixtures were significantly reduced by adding the additives of present Examples 1 and 3 to 5 (EA2, EA3, EA4, and EA5) or present Example 6 (EM2), EM0, and EA0 to the resin precursor composition of BAHF.
Although not listed in Table 1, viscosity reduction effect of the additives of Example 2 (EA1) and Examples 7, 8, 9, 10, and 11 (EM1, EM3, BA3, BA4, and BA5) was similarly confirmed to be equivalent to the viscosity reduction effect of the additives of Examples 1 and 6.

Example 25

Preparation of Cured Product (BAHF-EA2)

Of optical resin precursor of Example 12 (BAHF-EA2), the resin precursor composition having a composition ratio of BAHF:EA2:HCPK=90:10:0.5 was irradiated with ultraviolet rays to prepare a resin composition BAHF-EA2 cured product having a thickness of 5 mm. In irradiation with ultraviolet light, an ultraviolet irradiation machine (UL-250, manufactured by HOYA CANDEO OPTRONICS Inc.) equipped with a high pressure mercury lamp generating ultraviolet rays having a wavelength of 365 nm was used and the resin precursor composition was irradiated as pre-curing through ground glass at 8 mW/cm$^2$ for 150 seconds (1,200 mJ/cm$^2$). The ground glass was removed and the pre-cured composition was further irradiated at 8 mW/cm$^2$ for 75 seconds (600 mJ/cm$^2$). Note that the light source such as a metal halide lamp, a high-pressure mercury lamp, and an LED can be used as long as the light source emits light having a wavelength of 365 nm. Subsequently, the irradiated composition was irradiated as main curing at 31 mW/cm$^2$ for 233 seconds (about 7,000 mJ/cm$^2$) using an ultraviolet light irradiator (manufactured by Eye Graphics Co., Ltd.) equipped with a metal halide lamp emitting ultraviolet light having a wavelength of 365 nm.

Example 26

Preparation of Cured Product (BAHF-EA0)

Each of the optical resin precursors (BAHF-EA0-Compound A) in Example 22 was irradiated with ultraviolet rays to prepare a cured product of the resin composition BAHF-EA0 having a thickness of 5 mm. As irradiation with ultraviolet light, each of the resin compositions was irradiated as pre-curing through ground glass at 8 mW/cm$^2$ for 75 seconds (600 mJ/cm$^2$). The ground glass was removed and the pre-cured composition was further irradiated at 8 mW/cm$^2$ for 150 seconds (1,200 mJ/cm$^2$). Subsequently, an ultraviolet light irradiator (manufactured by Eye Graphics Co., Ltd.) equipped with a metal halide lamp emitting ultraviolet light having a wavelength of 365 nm was used and the irradiated composition was irradiated as main curing at 31 mW/cm$^2$ for 583 seconds (about 18,000 mJ/cm$^2$).

Example 27

Preparation of Cured Product (BAHF-EM0)

The same (or similar) process as the process in Example 22 above was carried out to the optical resin precursors (BAHF-EM0-Compound A) in Example 23 to prepare a cured product of the resin composition BAHF-EM0 having a thickness of 5 mm.

Comparative Example 2

Preparation of Cured Product (BAHF)

The optical resin precursor composition (BAHF) prepared in Comparative Example 1 was irradiated with ultraviolet rays to prepare a cured product of the resin composition BAHF having a thickness of 5 mm. As irradiation with ultraviolet light, each of the resin compositions was irradiated as pre-curing through ground glass at 8 mW/cm$^2$ for 150 seconds (1,200 mJ/cm$^2$). The ground glass was removed and the pre-cured composition was further irradiated at 8 mW/cm² for 75 seconds (600 mJ/cm²). Subsequently, an ultraviolet light irradiator (manufactured by Eye Graphics Co., Ltd.) equipped with a metal halide lamp emitting ultraviolet light having a wavelength of 365 nm was used and the irradiated composition was irradiated as main curing at 31 mW/cm² for 233 seconds (about 7,000 mJ/cm²).

<Measurement of Refractive Index of Optical Resin Precursor Composition>

The refractive indices of the cured products to g line, F line, and d line were measured at 22.5° C. using a refractometer (Type PR-2) manufactured by Carl Zeiss Jena GmbH. The results are listed in Table 2.

TABLE 2

|  | ng | nF | nd | vd |
|---|---|---|---|---|
| Example 25 | 1.5479 | 1.5391 | 1.5287 | 36.0 |
| Example 26 | 1.5480 | 1.5394 | 1.5291 | 36.2 |
| Example 27 | 1.5475 | 1.5388 | 1.5285 | 36.4 |
| Comparative Example 2 | 1.5479 | 1.5390 | 1.5285 | 35.5 |

Figure 4:
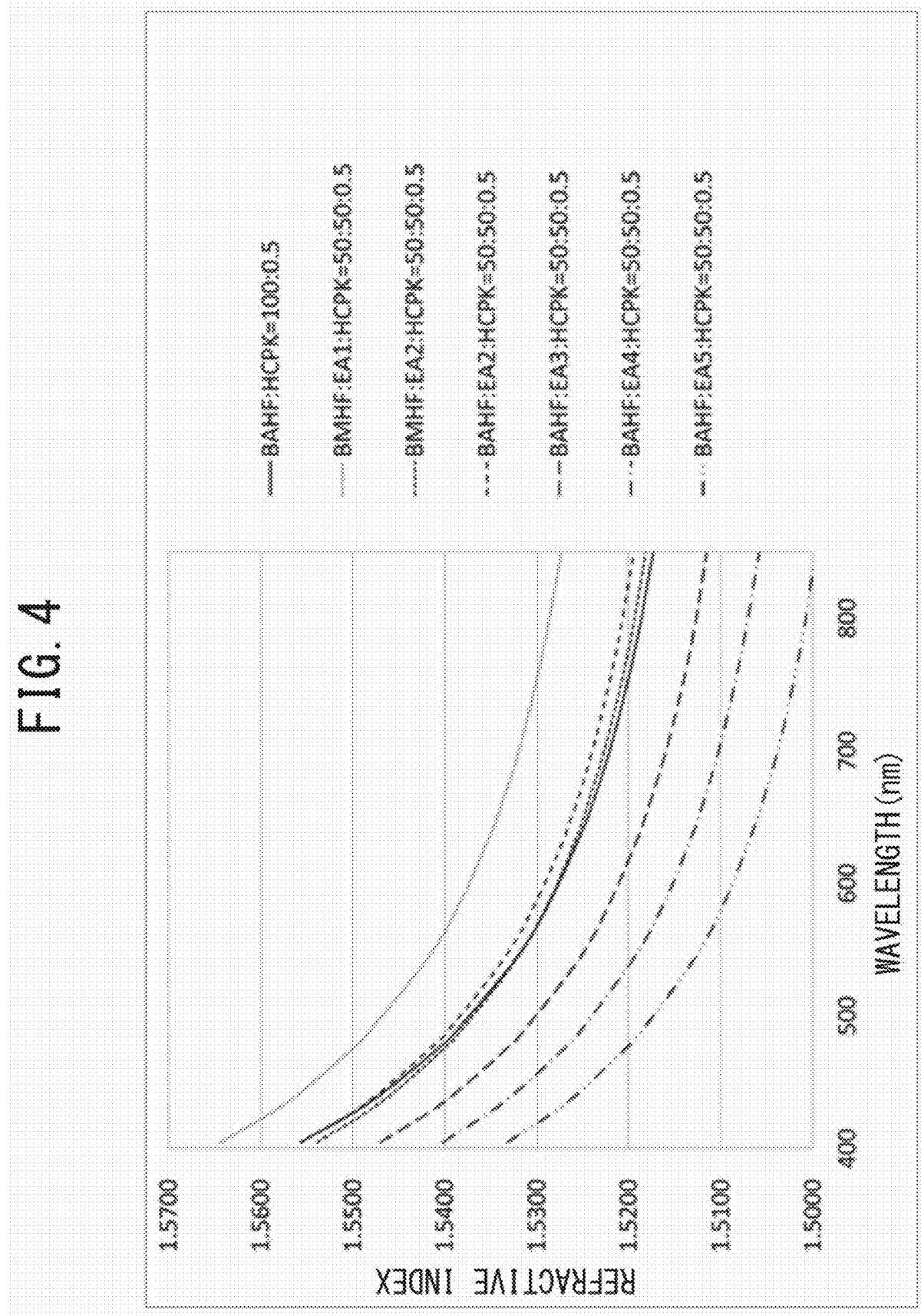
FIG. 4 is a graph of measurement results of the refractive index-wavelength characteristics of a cured product of the optical resin precursor composition according to the embodiment of the present invention.

FIG. 4 illustrates the refractive index wavelength characteristics of the optical resin precursor composition cured products prepared in the same (or similar) manner as described above by adding each of EA1, EA2, EA3, EA4, and EA5 synthesized in Examples 1 to 5 to BAHF or BMHF as additives in the following compositions.

| Composition ratio | Abbe number vd |
|---|---|
| BMHF:EA1:HCPK (50:50:0.5 parts by mass) | 37.4 |
| BMHF:EA2:HCPK (50:50:0.5 parts by mass) | 38.0 |
| BAHF:EA2:HCPK (50:50:0.5 parts by mass) | 37.9 |
| BAHF:EA3:HCPK (50:50:0.5 parts by mass) | 37.8 |
| BAHF:EA4:HCPK (50:50:0.5 parts by mass) | 38.5 |
| BAHF:EA5:HCPK (50:50:0.5 parts by mass) | 38.9 |

Figure 5:
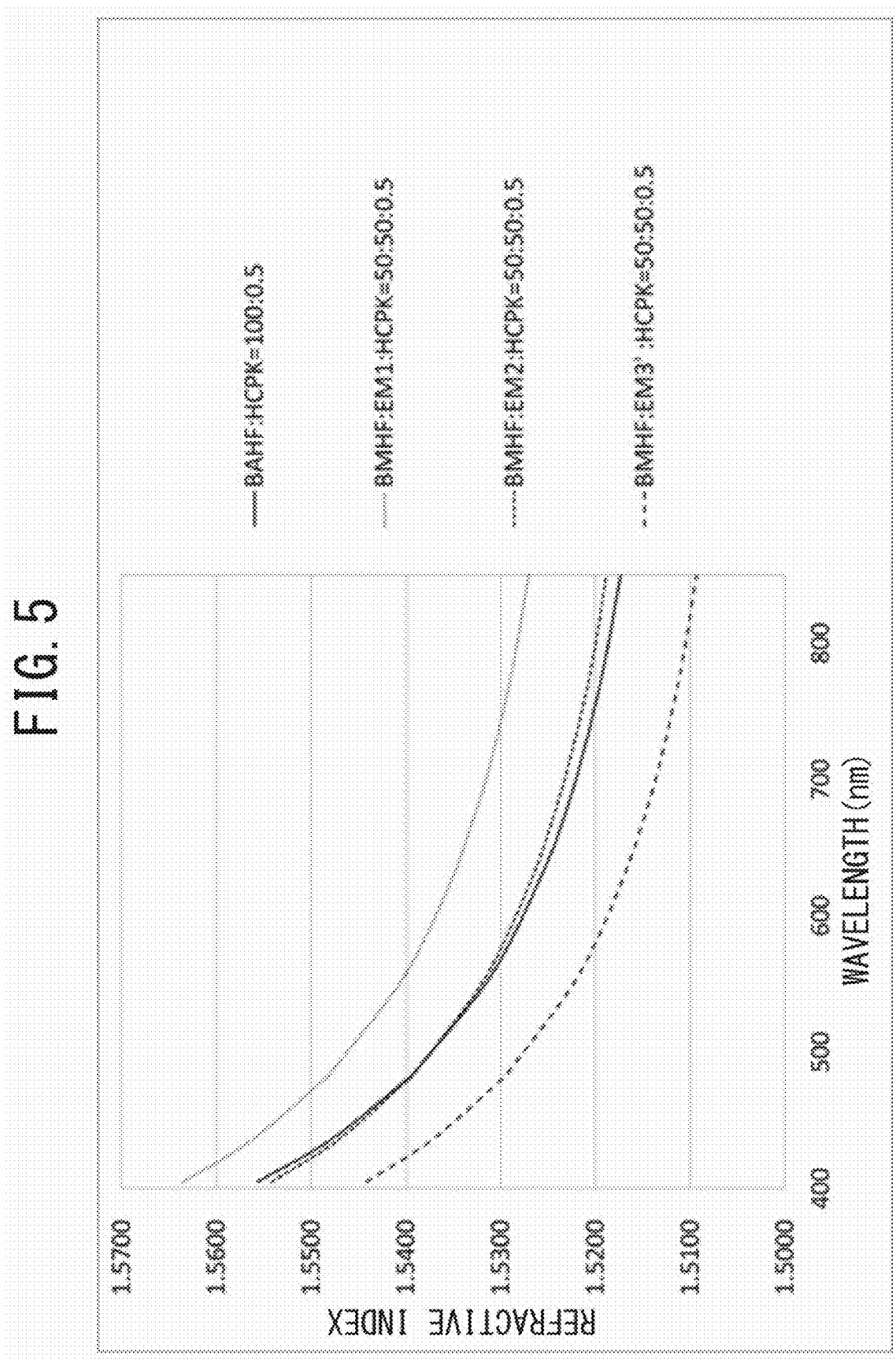
FIG. 5 is a graph of measurement results of the refractive index-wavelength characteristics of the cured product of the optical resin precursor composition according to the embodiment of the present invention.

FIG. 5 illustrates the refractive index wavelength characteristics of the optical resin precursor composition cured products prepared in the same (or similar) manner as described above by adding each EM1, EM2, and EM3 synthesized in Examples 6 to 8 to BAMF as additives in the following compositions.

| Composition ratio | Abbe number vd |
|---|---|
| BMHF:EM1:HCPK (50:50:0.5 parts by mass) | 37.9 |
| BMHF:EM2:HCPK (50:50:0.5 parts by mass) | 38.6 |
| BMHF:EM3:HCPK (50:50:0.5 parts by mass) | 38.5 |

Example 28

Preparation of Diffractive Optical Element 1

A diffractive optical element was prepared by using the optical resin precursor composition having a composition ratio of BAHF:EA2:HCPK (90:10:0.5 parts by mass) in the optical resin precursor compositions prepared in Example 12 above as the first diffractive optical component (the low refractive index and high dispersion resin) 1 and the resin precursor composition of Michael addition reaction product of tricyclodecanedimethanol diacrylate (A-DCP) and di(2-mercaptodiethyl)sulfide (DMDS) (A-DCP:DMDS=88:12) and HCPK (100:0.5 parts by mass) prepared as the second diffractive optical component (the high refractive index and low dispersion resin) 2 illustrated in FIG. 1.

First, the optical resin precursor composition having a composition ratio of BAHF:EA2:HCPK (90:10:0.5) was dropped onto a glass substrate as the optical resin precursor composition (the low refractive index and high dispersion resin) 1 prepared as the first optical component illustrated in FIG. 1. Thereafter, the predetermined mold was brought close to the resin surface and brought close to the glass substrate to a position where the resin thickness was reached to 200 μm to spread the resin. The spread resin was irradiated with ultraviolet rays. The ultraviolet ray irradiation was carried out using an ultraviolet ray irradiation machine (UL-250, manufactured by HOYA CANDEO OPTRONICS Corporation) having a high pressure mercury lamp emitting ultraviolet light having a wavelength of 365 nm. At this time, the spread resin was irradiated as pre-curing through ground glass at 6 mW/cm² for 167 seconds (1,000 mJ/cm²). The ground glass was removed and the pre-cured composition was further irradiated at 7 mW/cm² for 14 seconds (100 mJ/cm²). The light source such as a metal halide lamp, a high-pressure mercury lamp, an LED, and the like can be used as long as the light source emits light having a wavelength of 365 nm. After the pre-curing, the pre-cured product was removed from the mold to prepare the first diffractive optical component. Here, the viscosity of the resin precursor used for the first optical component was 3,900 mPa·s, which is sufficiently low.

Subsequently, the resin precursor composition of the Michael addition reaction product of tricyclodecanedimethanol diacrylate (A-DCP) and di(2-mercaptodiethyl)sulfide (DMDS) (A-DCP:DMDS=88:12 parts by mass):HCPK (100:0.5 parts by mass) as the optical resin precursor composition (the high refractive index and low dispersion resin) 2 prepared as the second diffractive optical component illustrated in FIG. 1 was applied onto the molded first diffractive optical component. Thereafter, the mold the surface of which was processed in a flat plate shape was brought close to the applied resin surface and the base lens was slowly brought close to a position where the resin thickness was reached to 300 μm to spread the resin. Thereafter, the spread resin was irradiated with ultraviolet rays. The ultraviolet ray irradiation conditions carried out as the pre-curing were the same as (or similar to) the conditions of the pre-curing for the first optical component. First, the spread resin was irradiated as pre-curing through ground glass at 6 mW/cm² for 167 seconds (1,000 mJ/cm²). The ground glass was removed and the pre-cured composition was further irradiated at 7 mW/cm² for 14 seconds (100 mJ/cm²). Thereafter, the mold was released from the resin and the irradiated resin was irradiated as main curing at 20 mW/cm² for 500 seconds (10,000 mJ/cm²) using an ultraviolet light irradiator (manufactured by Eye Graphics Co., Ltd.) equipped with a metal halide lamp emitting ultraviolet light having a wavelength of 365 nm to mold a diffractive optical element. The grating height of the diffraction grating was 28.2 μm.

Example 29

Preparation of Diffractive Optical Element 2

A diffractive optical element was prepared in a process the same as (or similar to) the process in Examples 28 using a composition having a composition ratio of BAHF:EA2:

Compound A:HCPK (85:12:3:0.5 parts by mass) prepared in Example 22 instead of the low refractive index and high dispersion resin precursor composition having a composition ratio of BAHF:EA2:HCPK (90:10:0.5 parts by mass) in Example 28, using a Michael addition reaction product of tricyclodecanedimethanol diacrylate (A-DCP) and di(2-mercaptodiethyl)sulfide (DMDS) (A-DCP:DMDS=88:12 parts by mass):HCPK (100:0.5 parts by mass) instead of the high refractive index and low dispersion resin precursor composition in Example 28, and using a Michael addition reaction product of A-DCP and DMDS (A-DCP:DMDS=90:10):HCPK (100:0.5 parts by mass). The grating height of the diffraction grating was 28.1 µm. Here, the viscosity of the resin precursor used for the first optical component was 2,160 mPa·s, which was sufficiently low.

Example 30

Preparation of Diffractive Optical Element 3

A diffractive optical element was prepared in a process the same as (or similar to) the process in Example 28 using a composition having a composition ratio of BAHF:EM0 A:HCPK (85:12:3:0.5 parts by mass) prepared in Example 23 instead of the low refractive index and high dispersion resin precursor composition having a composition ratio of BAHF:EA2:HCPK (90:10:0.5 parts by mass) in Example 28 and using a Michael addition reaction product of tricyclodecanedimethanol diacrylate (A-DCP) and di(2-mercaptodiethyl)sulfide (DMDS) (A-DCP:DMDS=88:12 parts by mass):HCPK (100:0.5 parts by mass) instead of the high refractive index and low dispersion resin precursor composition in Example 28. Note that the grating height of the diffraction grating was 28.8 µm. Here, the viscosity of the resin precursor used for the first optical component was 1,960 mPa·s, which was sufficiently low.

Comparative Example 3

Preparation of Diffractive Optical Element 4

A diffractive optical element was prepared in the same process to the process in Example 28 using the optical resin precursor composition having a composition ratio of BAHF:HCPK (100:0.5 parts by mass) prepared in Comparative Example 1 instead of the resin precursor composition having a composition ratio of BAHF:EA2:HCPK (90:10:0.5 parts by mass) in Example 28. The grating height of the diffraction grating was 27.9 µm.

From the above results, the viscosity of the optical resin precursor composition is significantly lowered by adding the additive according to the present embodiment represented by general formula (1) to BAHF serving as the optical resin precursor composition having a low refractive index and high dispersion and thus a precise relief patterns were able to be obtained without problems at the time of processing the diffractive optical element. As for the additives of Examples 2 to 8, it was ascertained that the effect of lowering the viscosity was the same (or similar) the effect in Example 1 and precise relief patterns were able to be obtained without problems at the time of processing the diffractive optical elements. On the other hand, as a result of attempts to prepare a diffractive optical element by a method the same as (or similar to) the method in Examples described above, the resin precursor composition of Comparative Example 1 caused mixing of bubbles unless the speed of mold movement for contacting the mold with the resin was sufficiently lowered in the process of spreading the resin with the mold, compared with the molding process using the optical resin precursor to which the additive represented by general formula (1) was added.

Figure 6:
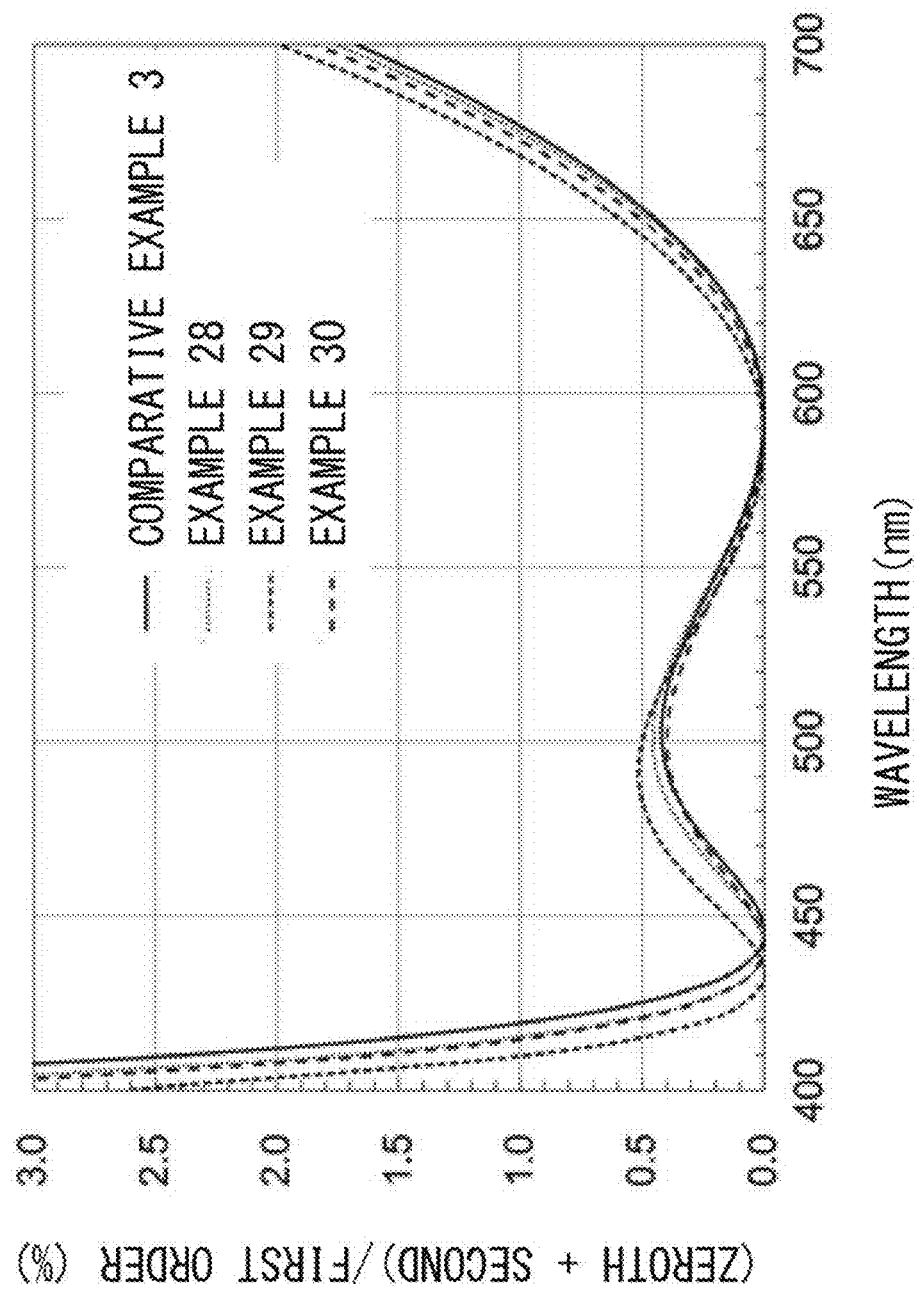
FIG. 6 is a graph of measurement results of a relationship between the light wavelength and the amount of flare for the contact multilayer diffractive optical element (DOE) according to the embodiment of the present invention.

Scalar calculation was carried out for a flare amount of each of the diffractive optical elements prepared in Examples 28 to 30 and Comparative Example 3. In FIG. 6, a graph of the relationship between the wavelength of light and the amount of flare is illustrated. In FIG. 6, the horizontal axis represents the wavelength of light (nm) and the vertical axis represents the ratio (%) of the sum of the zero-order diffracted light and the second order diffracted light to the first-order diffracted light.

Each dotted line in FIG. 6 illustrates the flare amount of the diffractive optical elements prepared by using each of the optical resin precursor compositions of Examples 12, 22, and 24 above. The solid line in FIG. 6 illustrates the flare amount of the diffractive optical element prepared by using the optical resin precursor composition of Comparative Example 2 above.

As illustrated, the amount of generated flare when the (meth)acrylate compound additive according to the present embodiment was added to the optical resin compound having a low refractive index and high dispersion properties was almost unchanged as compared with the case of BAHF alone. The amount of generated flare was also almost unchanged even when EM0, which is an additive and one of the compounds represented by general formula (1), was added.

In Examples 28 to 30, the copolymer of A-DCP and DMDS was used as the high refractive index and low dispersion resin. The resin, however, is not limited to this copolymer. Examples of the usable high refractive index and low dispersion resin include hexanediol di(meth)acrylate, decanediol di(meth)acrylate, dipropylene glycol di(meth)acrylate, and neopentyl glycol di(meth)acrylate. The resin on the high refractive index and low dispersion side can be used by appropriate selection and formulation in accordance with the refractive index characteristics illustrated in FIGS. 4 and 5. For example, the material that lowers the reflective index may be selected as the high refractive index and low dispersion resin serving as the counterpart resin with respect to the resin in which the formulation ratio of fluorine is high and the refractive index is low as a whole.

By adding the (meth)acrylate compound according to the present embodiment, the viscosity of the low refractive index and high dispersion resin is lowered to improve processing properties. In addition, by selecting the type and adjusting the amount to be added of the (meth)acrylate compound acting as the additive according to the embodiment of the present invention in accordance with the behavior of the selected high refraction and low dispersion resin, the degree of freedom of refractive index behavior adjustment with respect to the wavelength increases and more precise control of the wavelength-refractive index behavior is possible. Consequently, further flare light reduction effect can be expected.

<Thermal Property Evaluation of Diffractive Optical Element>

The physical properties of the low refraction and high dispersion resins and the high refractive index and low dispersion resins used in Examples 28 to 30 and Comparative Example 3 are listed below. Here, as described above, the thicknesses of the diffraction gratings of the first diffractive optical element and the second diffractive optical element are 200 µm and 300 µm, respectively. The diffraction grating height is about 28 µm.

Example 28

First diffractive optical component (low refractive index and high dispersion)

Cured product of BAHF:EA2:HCPK=(90:10:0.5 parts by mass)

Storage elastic modulus of cured product: 110 (MPa, at 100° C.)

Linear expansion coefficient of cured product: $1.0 \times 10^{-4}$ (1/K, 25° C. to 70° C.)

Second diffractive optical component (high refractive index and low dispersion)

Cured product of Michael addition reaction product of A-DCP:DMDS (88:12 parts by mass):HCPK=(100:0.5 parts by mass)

Storage elastic modulus of cured product: 91 (MPa, at 100° C.)

Linear expansion coefficient of cured product: $1.0 \times 10^{-4}$ (1/K, 25° C. to 70° C.)

Example 29

First diffractive optical component (low refractive index and high dispersion)

BAHF:EA2:Compound A:HCPK=(85:12:3:0.5 parts by mass)

Storage elastic modulus of cured product: 34 (MPa, at 100° C.)

Linear expansion coefficient of cured product: $1.8 \times 10^{-4}$ (1/K, 25° C. to 70° C.)

Second diffractive optical component (high refractive index and low dispersion)

Michael addition reaction product of A-DCP:DMDS (90:10 parts by mass):HCPK=(100:0.5 parts by mass)

Storage elastic modulus of cured product: 177 (MPa, at 100° C.)

Linear expansion coefficient of cured product: $0.9 \times 1.0^{-4}$ (1/K, 25° C. to 70° C.)

Example 30

First diffractive optical component (low refractive index and high dispersion)

BAHF:EM0:Compound A:HCPK=(85:12:3:0.5 parts by mass)

Storage elastic modulus of cured product: 48 (MPa, at 100° C.)

Linear expansion coefficient of cured product: $1.1 \times 10^{-4}$ (1/K, 25° C. to 70° C.)

Second diffractive optical component (high refractive index and low dispersion)

Michael addition reaction product of A-DCP:DMDS (83:17 parts by mass):HCPK (100:0.5 parts by mass)

Storage elastic modulus of cured product: 90 (MPa, at 100° C.)

Linear expansion coefficient of cured product: $1.1 \times 10^{-4}$ (1/K, 25° C. to 70° C.)

Comparative Example 3

First diffractive optical component (low refractive index and high dispersion)

BAHF:EA2:Compound A:HCPK=(85:12:3:0.5 parts by mass)

Storage elastic modulus of cured product: 34 (MPa, at 100° C.)

Linear expansion coefficient of cured product: $1.8 \times 10^{-4}$ (1/K, 25° C. to 70° C.)

Second diffractive optical component (high refractive index and low dispersion)

Michael addition reaction product of A-DCP:DMDS (80:20 parts by mass):HCPK (100:0.5 parts by mass)

Storage elastic modulus of cured product: 8 (MPa, at 100° C.)

Linear expansion coefficient of cured product: $2.5 \times 10^{-4}$ (1/K, 25° C. to 70° C.)

A film of an inorganic oxide made of a multilayer film was deposited on the surface of each of the four diffractive optical elements prepared in Example 28 to 30 and Comparative Example 3 by a vacuum evaporation method to form an antireflection film. As a result, in the diffractive optical elements produced using the resins in Examples 28 to 30 having a linear expansion coefficient of $2.0 \times 10^{-4}$ (1/K, 25° C. to 70° C.) or lower, no cracks were generated in the film and a film having excellent antireflection properties was able to be formed. The diffractive optical elements in Examples 28 to 30 made of the cured products having a storage elastic modulus at 100° C. of 50 MPa or higher acting as the second diffractive optical components generated no wrinkles in the films even when environmental tests including a heat resistance test, a temperature cycle test, and a moisture resistance test were carried out. This means that the deformation of the resin surface due to stress of the film can be reduced because the storage elastic modulus of the resin (second optical component) closest to the air layer at 100° C. is 90 MPa or higher, which is high modulus, in Examples 28 to 30 even when the storage elastic modulus is somewhat lowered due to heating and moisture absorption.

On the other hand, when the same (or similar) environmental tests were carried out for the diffractive optical element produced in Comparative Example 3, a problem of generating wrinkles in the film arose. This is considered to be the result of resin surface deformation due to stress that the film has because the storage elastic modulus of the second diffractive optical component in Comparative Example 3 at 100° C. is 8 MPa, which is low modulus.

Here, use of a resin having a storage elastic modulus at 100° C. of 19 MPa for the second optical component enabled an antireflection film that did not generate wrinkles after environmental tests to be formed. Therefore, the antireflection film can be formed as long as the storage elastic modulus of the second diffractive optical component resin at 100° C. is at least 19 MPa or higher. In consideration of the effects of the size of the diffractive optical component (the area of the diffractive optical component surface) and the fluctuation of cured state distribution of the resin in the diffractive optical component surface, however, higher storage elastic modulus is preferable. The storage elastic modulus is preferably 50 MPa or higher by multiplying a factor of safety.

In the diffractive optical elements of Examples 28 to 30, the thickness of the second optical component is constant regardless of the location, that is, the second optical component has the equal thickness. The second optical component, however, may have an aspherical surface shape by varying the thickness of the second optical component depending on the location in the radius direction. The diffractive optical element having the aspherical lens function in the second optical component in addition to the functions of the diffractive optical element can provide further significant contribution of reduction in size and weight of the optical system. In the case where the aspherical lens is formed, thickness difference of the resin of the second diffractive optical component may be nearly equal to the thickness difference of the resin in the common composite aspherical lens. Specifically, the resin thickness difference between the thickest portion and the thinnest portion may be set to 10 µm or larger and 1,500 µm or smaller. As described above, change in the resin thickness of the second optical component depending on the location tends to increase the risks of generation of cracks during formation of the multilayer film on the surface and generation of wrinkles in the environmental tests. However, both of the first diffractive optical component and the second diffractive optical component according to the present invention have linear expansion coefficients of $2.0 \times 10^{-4}$ (1/K, 25° C. to 70° C.) or lower, which are low coefficients, and the second diffractive optical element has a storage elastic modulus at 100° C. of 50 MPa or higher, which is high modulus. Consequently, the optical element having no problems of cracks or wrinkles in the film and high environmental resistance can be prepared even when the second diffractive optical component has the aspherical surface shape formed by varying the thickness. Diffractive optical components having a linear expansion coefficient of $1.2 \times 10^{-4}$ (1/K, 25° C. to 70° C.) or lower allows the diffractive optical component having a spherical or aspherical lens shape having a resin thickness difference of 1,000 µm or larger to be stably molded.

From the above results, according to the additive according to the embodiment of the present invention, the processing properties can be improved without impairing the optical properties.

REFERENCE SIGNS LIST

1 First diffractive optical component
2 Second diffractive optical component
5 Relief pattern
51 Image-taking device
52 Camera body
53 Lens barrel
54 Image-taking lens
55 Sensor chip

What is claimed is:

1. A (meth)acrylate compound represented by general formula (1):

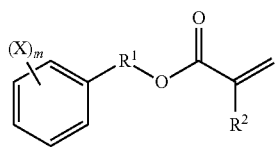
(1)

wherein, in the general formula (1),
each X independently represents a fluorine atom or a methyl group in which at least one hydrogen atom is substituted with a fluorine atom;
m represents 0;
$R^1$ represents an alkylene group having a carbon number of 2 or of 4 to 8 or an oxyalkylene group having a carbon number of 1 to 8; and
$R^2$ represents a hydrogen atom or a methyl group.

2. An additive for an optical resin comprising a (meth) acrylate compound represented by general formula (1):

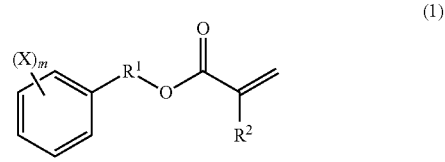
(1)

wherein, in the general formula (1),
each X independently represents a fluorine atom or a methyl group in which at least one hydrogen atom is substituted with a fluorine atom;
m represents 0;
$R^1$ represents an alkylene group having a carbon number of 2 or of 4 to 8 or an oxyalkylene group having a carbon number of 1 to 8; and
$R^2$ represents a hydrogen atom or a methyl group.

3. A resin precursor composition comprising: bifunctional (meth)acrylate (A Component); monofunctional (meth)acrylate (B Component); and a photopolymerization initiator (C Component), wherein the B Component is a compound represented by general formula (1) below:

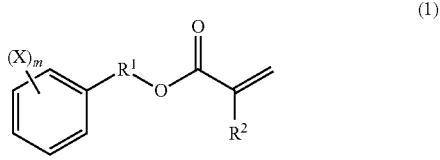
(1)

wherein, in the general formula (1),
each X independently represents a fluorine atom or a methyl group in which at least one hydrogen atom is substituted with a fluorine atom;
m represents 0;
$R^1$ represents an alkylene group having a carbon number of 2 or of 4 to 8 or an oxyalkylene group having a carbon number of 1 to 8; and
$R^2$ represents a hydrogen atom or a methyl group.

4. The resin precursor composition according to claim 3, wherein the A Component is a compound represented by general formula (6) below:

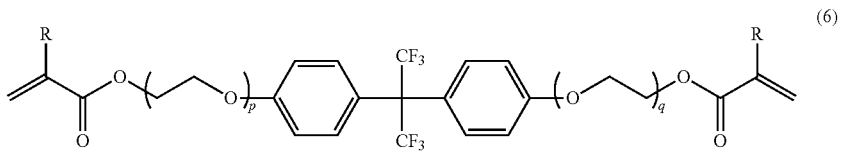
(6)

wherein, in the general formula (6) and the general formula (7), each R independently represents a hydrogen atom or a methyl group; p and q each independently represent an integer of 1 to 3; in the general formula (7), $R^4$ and $R^5$ each independently represent a hydrogen atom or an alkyl group having a carbon number of 1 to 2; and $R^6$, $R^7$, $R^8$, and $R^9$ each independently represent any one of a hydrogen atom, a fluorine atom, an alkyl group having a carbon number of 1 to 6, and a phenyl group in which one or some of hydrogen atoms are optionally substituted with an alkyl group having a carbon number of 1 to 6.

5. An optical resin composition comprising:
a constitutional unit represented by general formula (8):

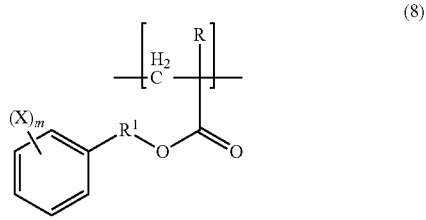

(8)

wherein, in the general formula (8),
each R independently represents a hydrogen atom or a methyl group;
each X independently represents a fluorine atom or a methyl group in which at least one hydrogen atom is substituted with a fluorine atom;
m represents 0; and
$R^1$ represents an alkylene group having a carbon number of 2 or of 4 to 8 or an oxyalkylene group having a carbon number of 1 to 8-8.

6. The optical resin composition according to claim 5, wherein the optical resin composition has a refractive index nd at d-line (587.56 nm) of 1.53 or smaller and an Abbe number νd of 39 or smaller.

7. The optical resin composition according to claim 5, wherein the optical resin composition has a storage elastic modulus at 100° C. of 50 MPa or higher.

8. The optical resin composition according to claim 5, wherein the optical resin composition has a linear expansion coefficient from 25° C. to 70° C. of $2.0 \times 10^{-4}$ (1/K) or lower.

9. An optical resin precursor composition comprising:
(a) the additive for an optical resin according to claim 2;
(b) an optical resin compound; and
(c) a photopolymerization initiator.

10. An optical element comprising:
a resin composition obtained by curing the optical resin composition according to claim 5.

11. An optical element comprising:
an optical resin composition obtained by curing the optical resin composition according to claim 5; and
an optical resin composition having a high refractive index and low dispersion compared with the obtained optical resin composition.

12. An optical device comprising
the optical element according to claim 10.

* * * * *

UNITED STATES PATENT AND TRADEMARK OFFICE
CERTIFICATE OF CORRECTION

PATENT NO. : 11,142,636 B2
APPLICATION NO. : 16/459923
DATED : October 12, 2021
INVENTOR(S) : Masakatsu Kasuya et al.

Page 1 of 1

It is certified that error appears in the above-identified patent and that said Letters Patent is hereby corrected as shown below:

In the Claims

Column 38, Line 4:
In Claim 5, delete "1 to 8-8." and insert --1 to 8.--, therefor Signed and Sealed this
Eighteenth Day of January, 2022

Drew Hirshfeld
*Performing the Functions and Duties of the*
*Under Secretary of Commerce for Intellectual Property and*
*Director of the United States Patent and Trademark Office*